United States Patent [19]

Markland, Jr. et al.

[11] Patent Number: 5,260,060
[45] Date of Patent: Nov. 9, 1993

[54] FIBRINOLYTIC ENZYMES

[75] Inventors: Francis S. Markland, Jr., Northridge; Anastassios D. Retzios, Los Angeles, both of Calif.

[73] Assignee: University of Southern California, Los Angeles, Calif.

[21] Appl. No.: 743,009

[22] Filed: Aug. 9, 1991

[51] Int. Cl.$^5$ .............................................. A61K 37/54
[52] U.S. Cl. ................... 424/94.67; 435/219
[58] Field of Search ..................... 424/94.67; 435/219

[56] References Cited

U.S. PATENT DOCUMENTS

| | | | |
|---|---|---|---|
| 3,983,002 | 9/1976 | Ohya et al. | 435/209 |
| 4,164,447 | 8/1979 | Fleming et al. | 435/193 |
| 4,610,879 | 9/1986 | Markland, Jr. et al. | 424/94.67 |

OTHER PUBLICATIONS

Molina et al. BA121594 (1990).
Chen et al., Toxicon 29(6)683–694 (1991).
Willis et al., "Purification and Biochemical Characterization of Atroxase, a Nonhemorrhagic Fibrinolytic Protease From Western Diamondback Rattlesnake Venom", *Biochemistry,* 1988, 27, 4769–4777.
Willis et al., "Thrombolysis With a Snake Venom Protease in a Rat Model of Venous Thrombosis", *Thrombosis Research,* (1989) 53: 19–29.

*Primary Examiner*—Douglas W. Robinson
*Assistant Examiner*—Jean C. Witz
*Attorney, Agent, or Firm*—Robbins, Berliner & Carson

[57] ABSTRACT

Novel fibrinolytic zinc metalloproteinases exhibiting direct fibrinolytic activity in plasminogen free systems, no detectable plasminogen activation activity in vitro, and no observable systemic toxicity in vivo as exemplified by the absence of hemorrhagic activity, characterized by peptide bond cleavage specificities which are markedly different from those of the heretofore identified metalloproteinases. Several of the enzymes are further characterized by substantially reduced proteolytic activity (as measured by azocaseinolytic activity in vitro) relative to *A.c.contortrix* fibrolase. The novel fibrinolytic enzymes with reduced proteolytic activity generally exhibit levels of proteolytic activity less than about 70% of that exhibited by a fibrinolytic enzyme having the activity profile of the enzyme as isolated from *A.c.contortrix* venom.

9 Claims, 21 Drawing Sheets

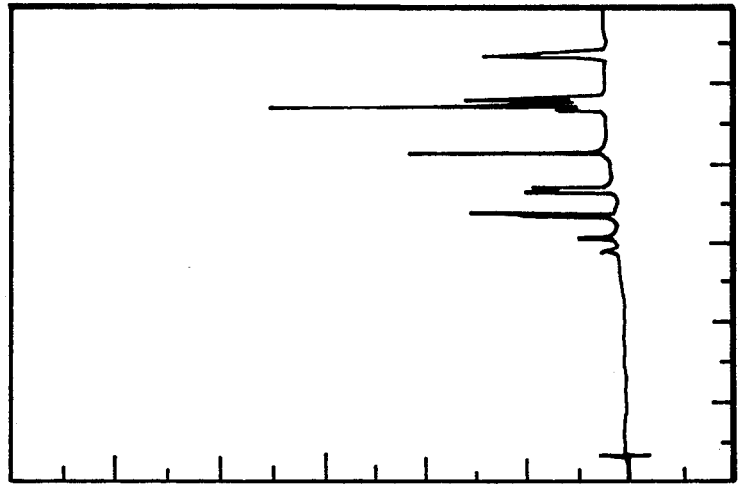
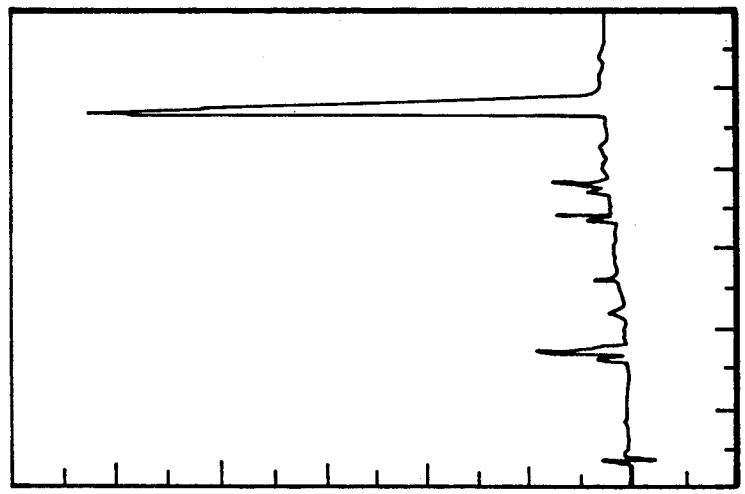
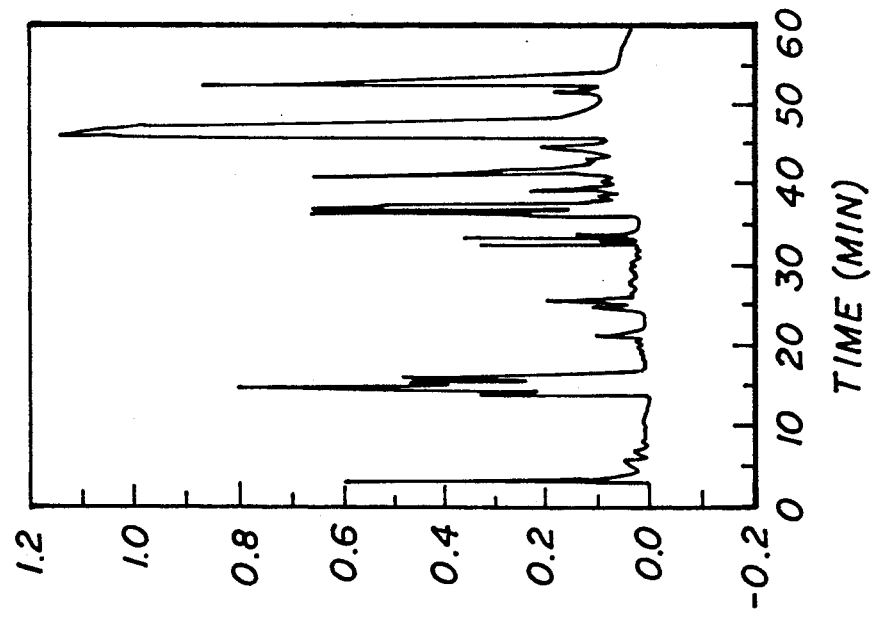

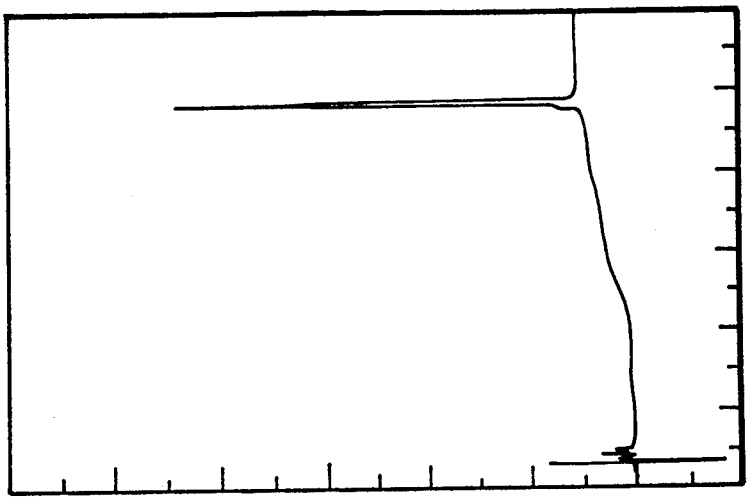
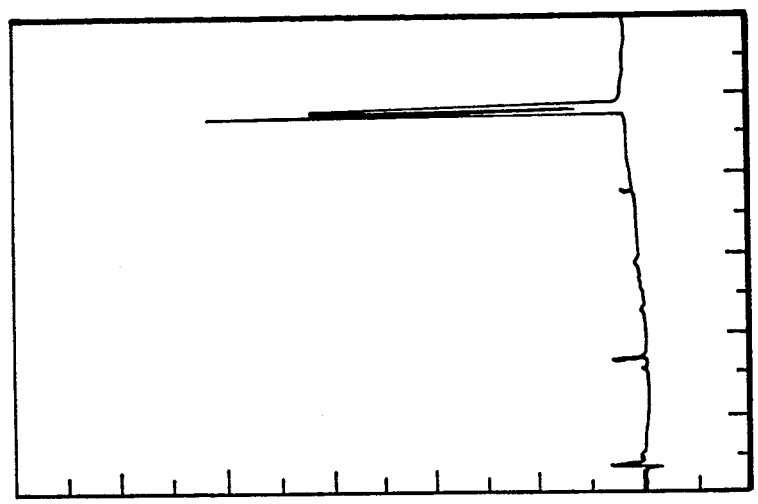
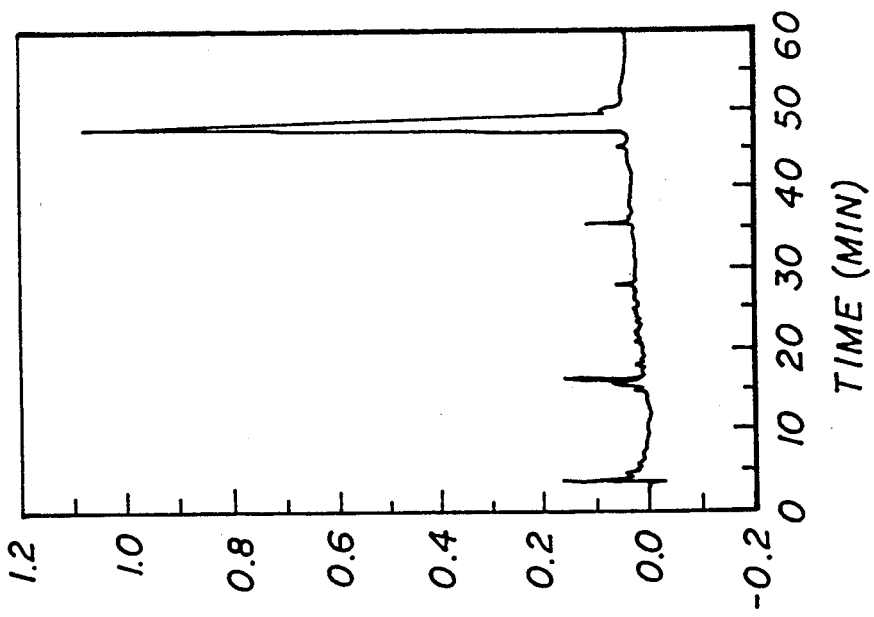

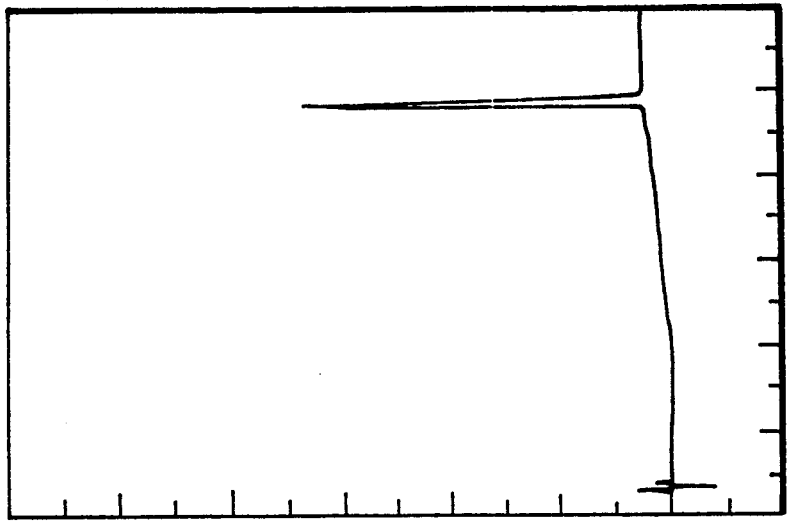
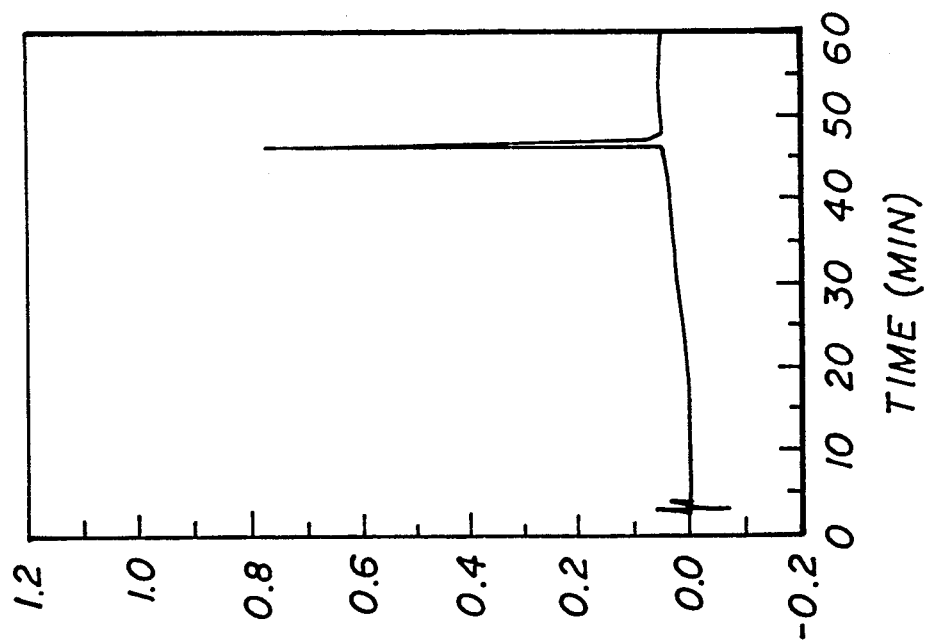

FIG. 5

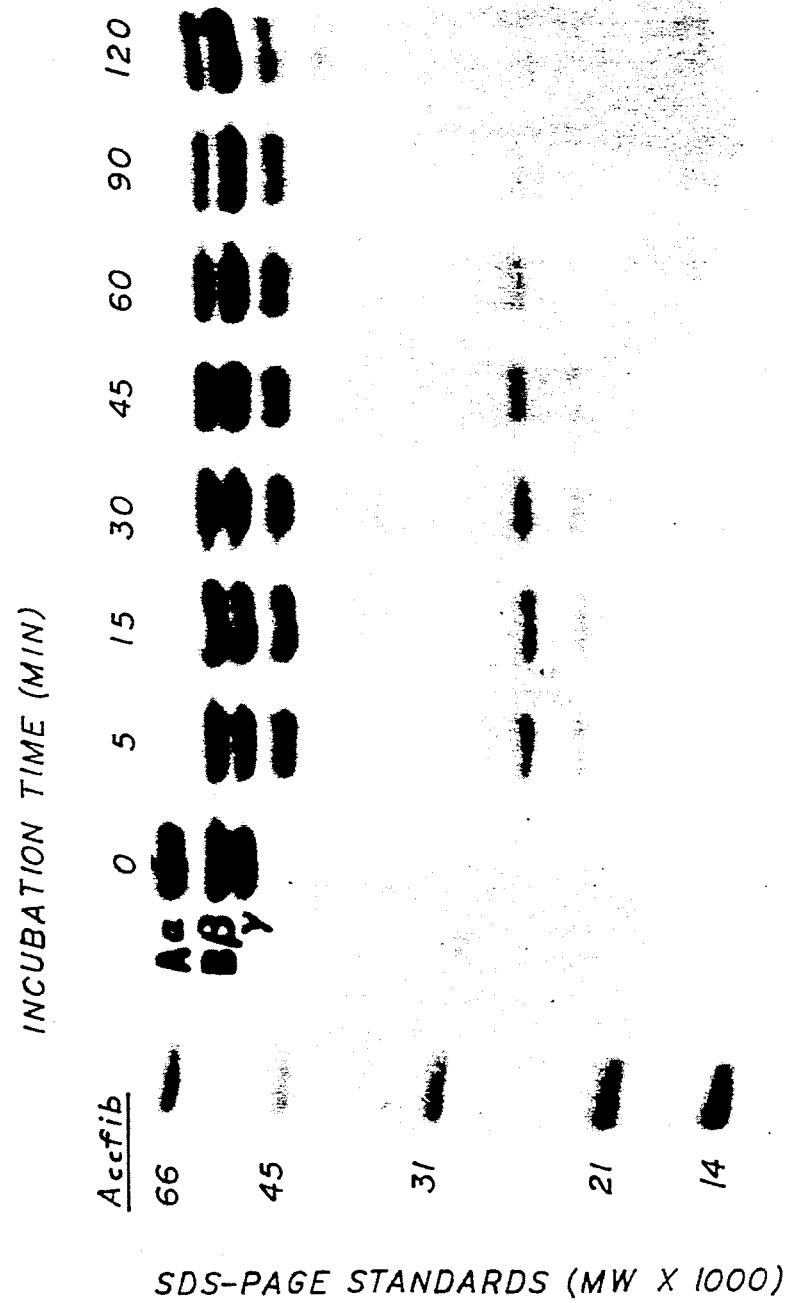

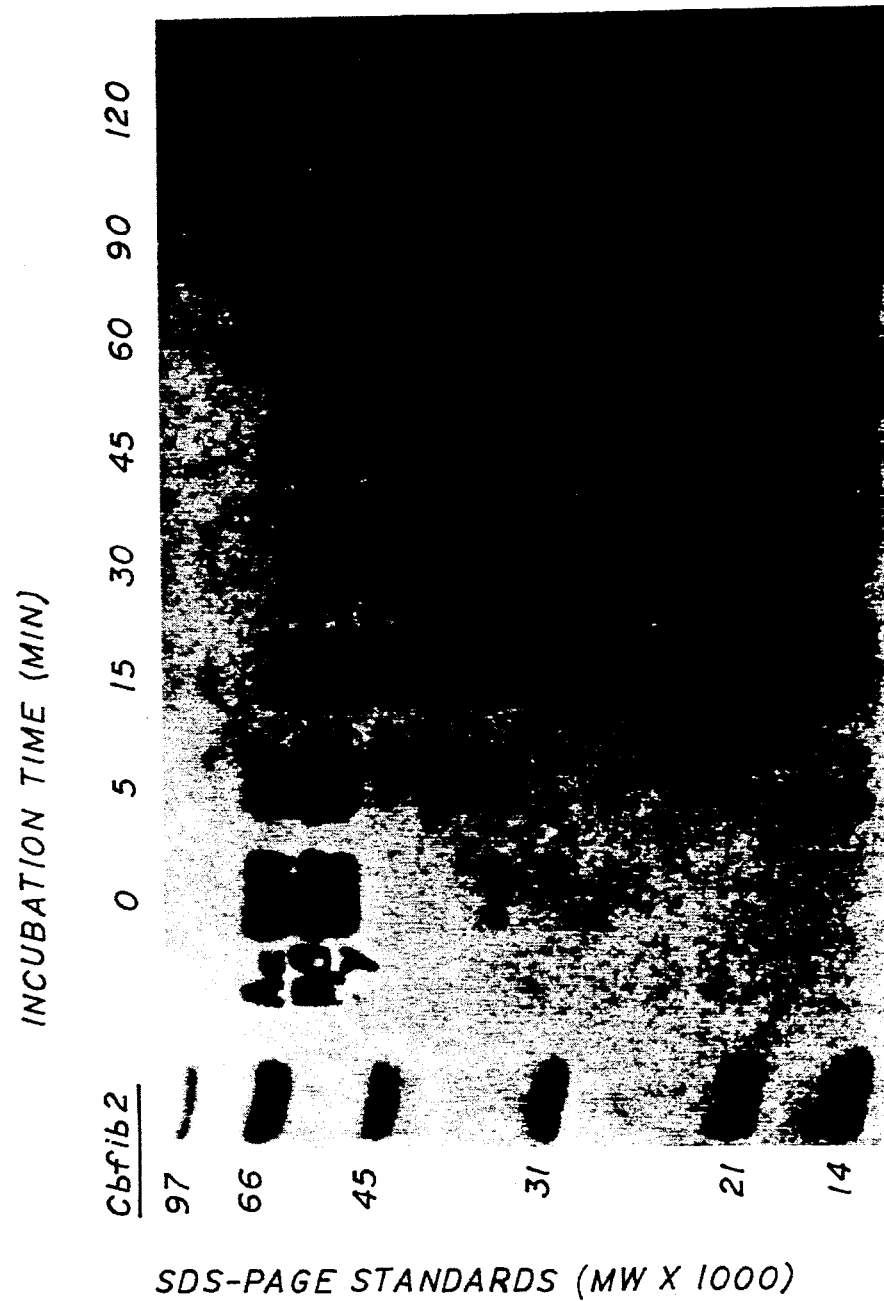
FIG. 8A(2)

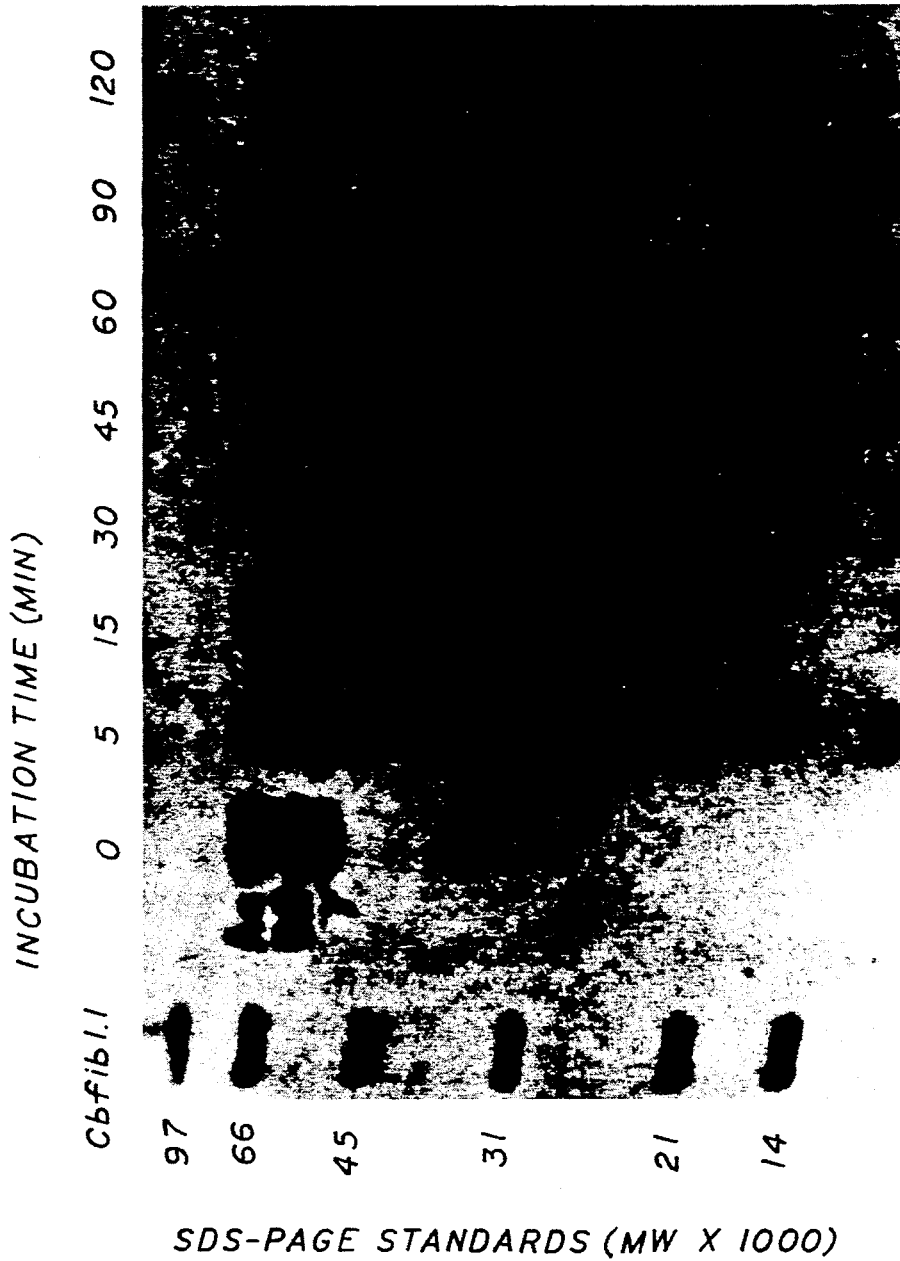

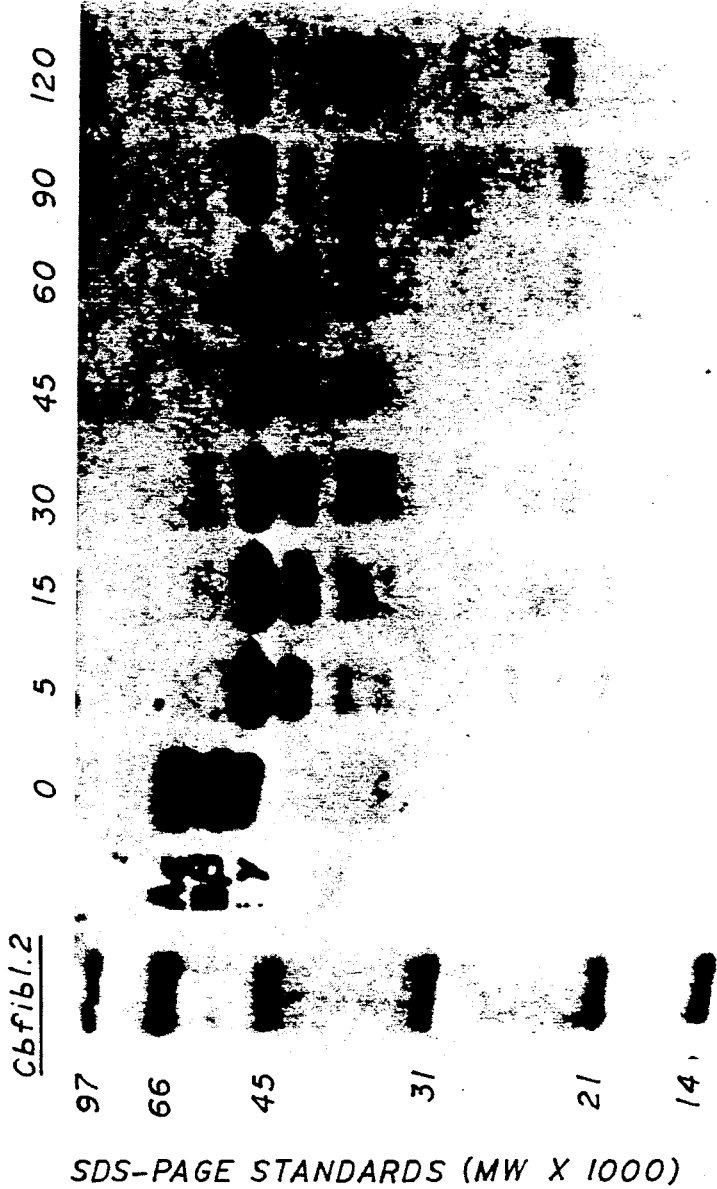

FIG. 8B(1)

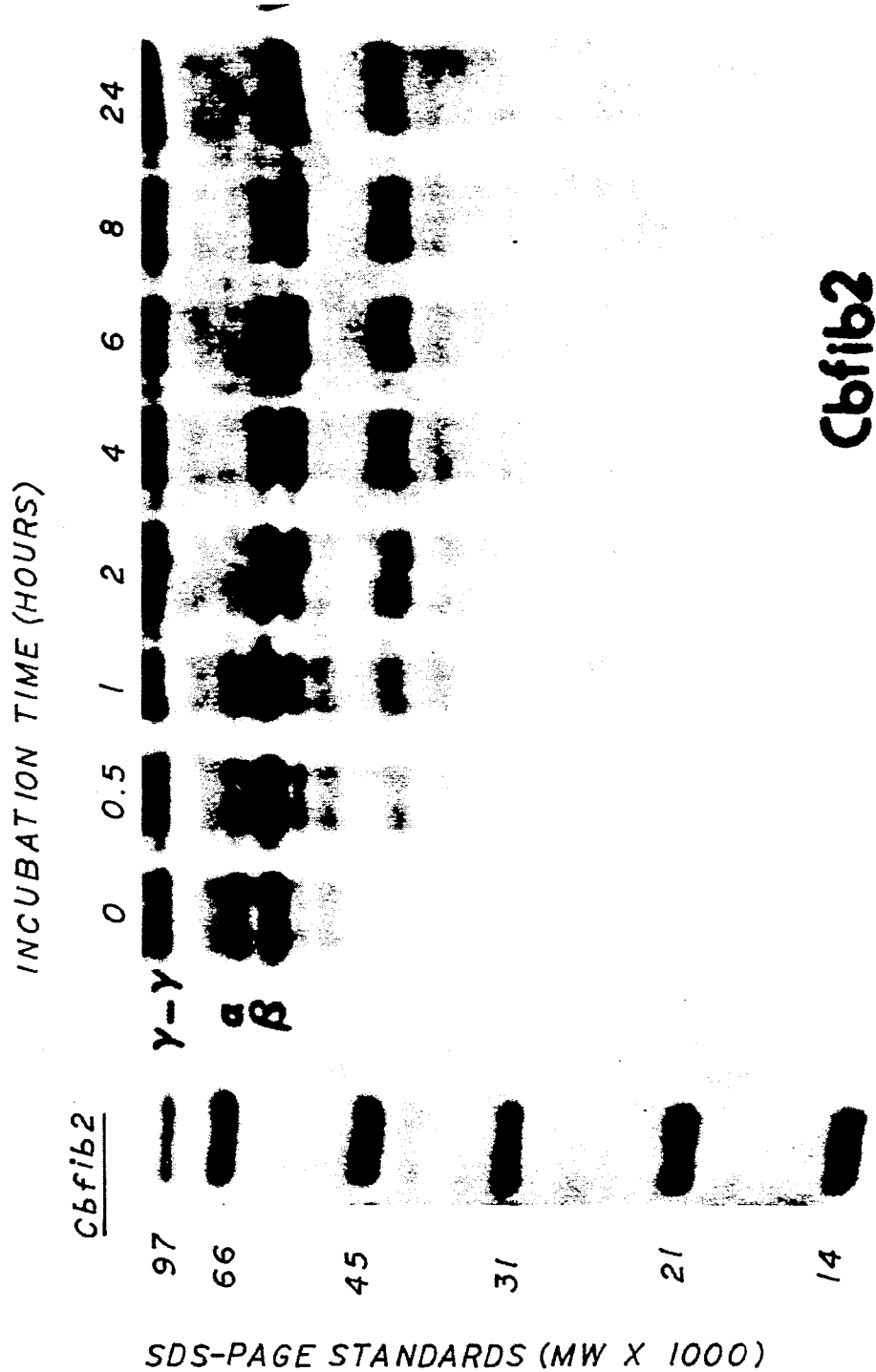

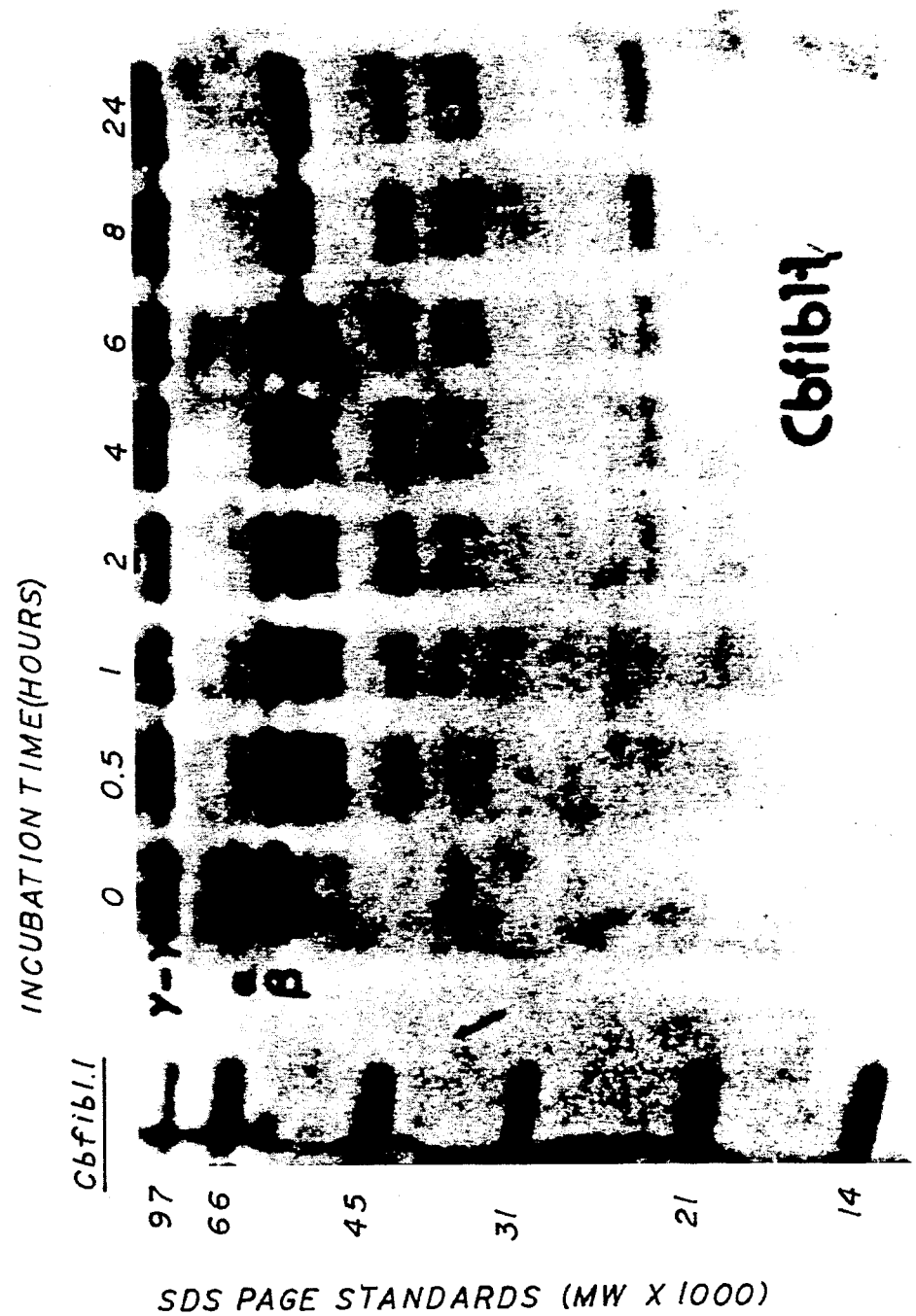
FIG. 8B(3)

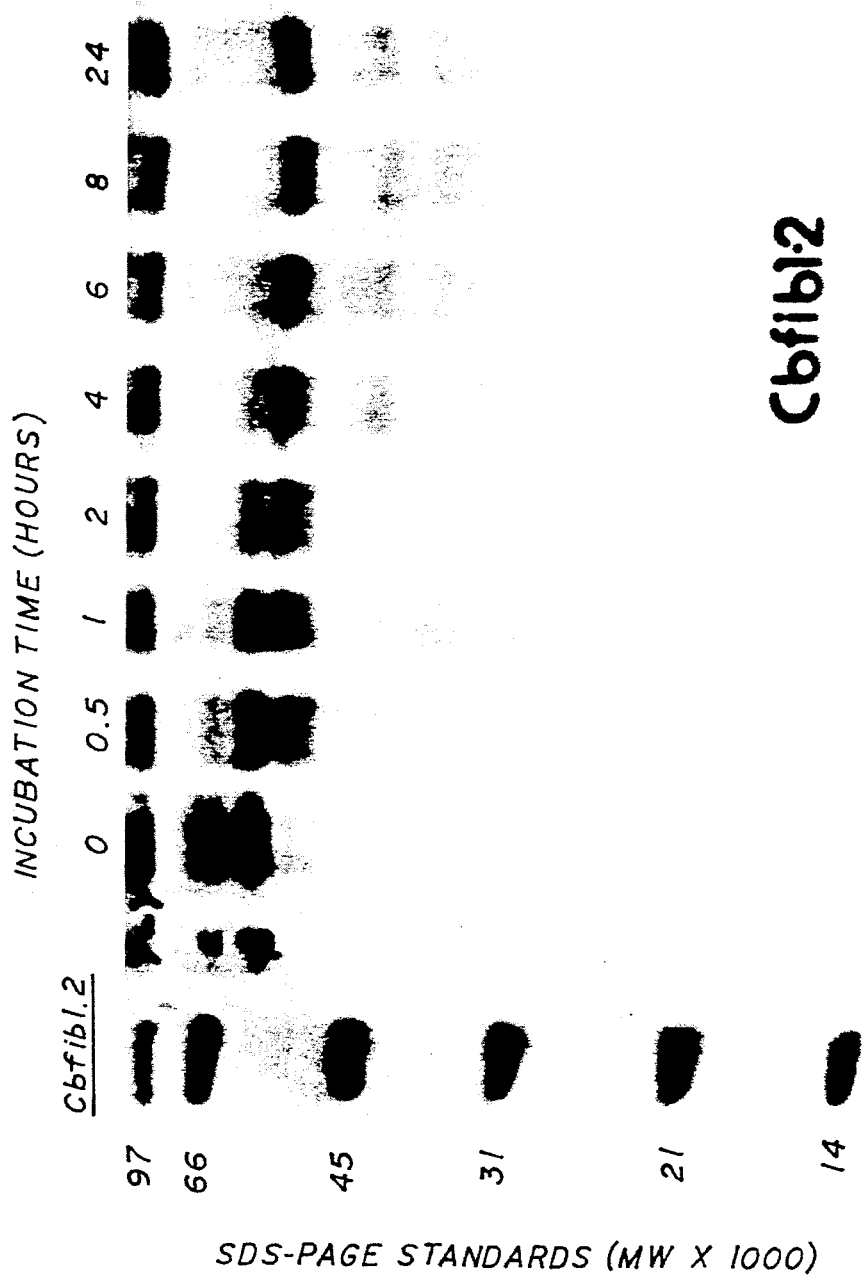

TIME (MIN)

TIME (MIN)

FIG. IIA
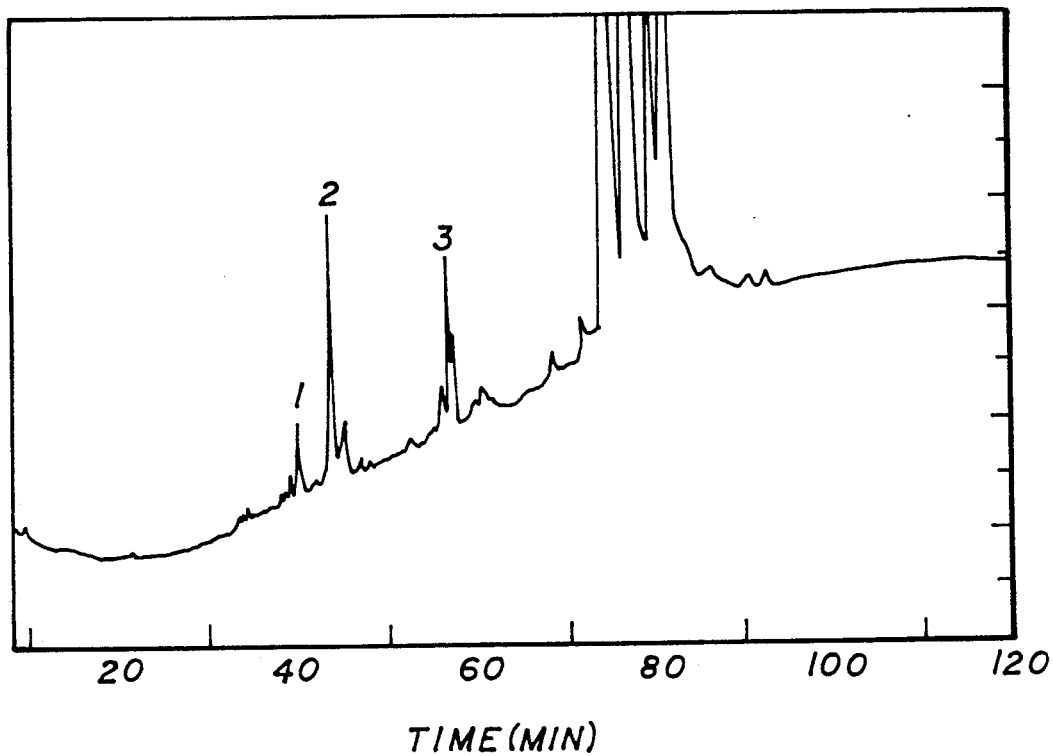
TIME (MIN)
FIG. IIB
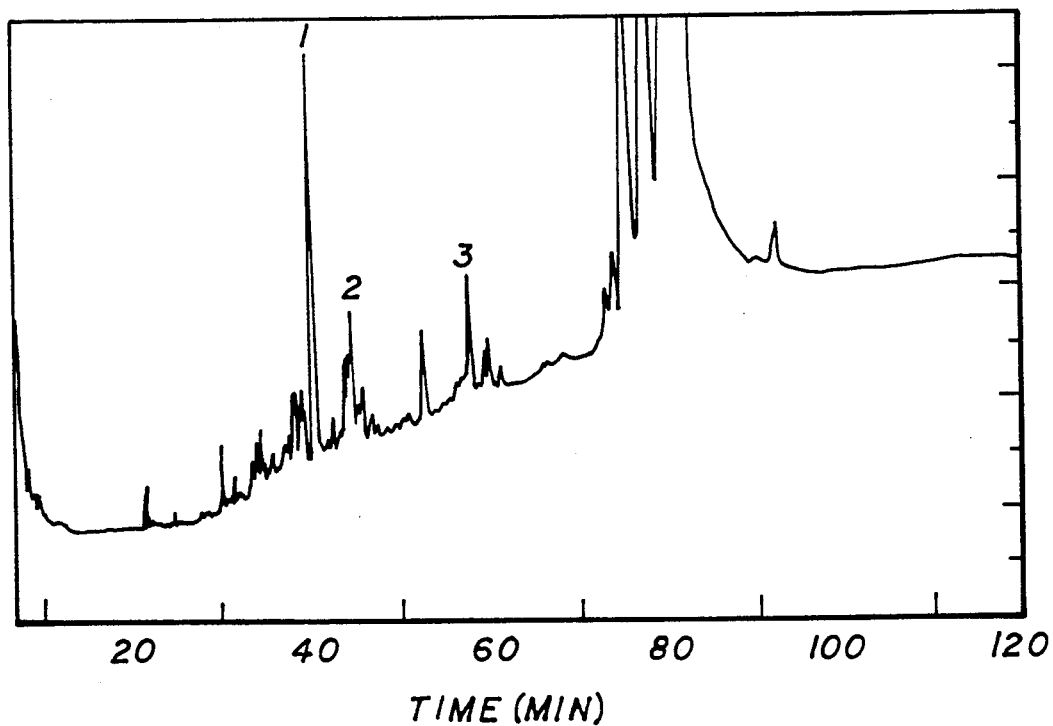
TIME (MIN)

FIBRINOLYTIC ENZYMES

BACKGROUND OF THE INVENTION

This invention relates to the field of protein chemistry, and more particularly, to the field of fibrinolytic enzymes.

A number of enzymes that influence blood coagulation have been isolated from various snake venoms. These enzymes can either promote or inhibit coagulation. Fibrinolytic activities have received special attention because of their possible therapeutic role.

U.S. Pat. No. 4,610,879 (the entire disclosure of which is hereby incorporated by reference) describes the isolation and purification of a fibrinolytic enzyme (fibrolase or Accfib) from the venom of *Agkistrodon contortrix contortrix* (Southern copperhead snake). This enzyme has been of great potential therapeutic interest in view of its direct fibrinolytic activity which is not readily inhibited by serum antiprotease when employed in vivo. Unlike urokinase and streptokinase, which operate by the conversion of plasminogen to the proteolytic enzyme plasmin, *A.c.contortrix* fibrolase is not a plasminogen activator. Plasmin degrades other plasma proteins, as well as fibrin clots. When plasmin forced by a plasminogen activator exceeds the capacity of the circulating plasmin inhibitor, alpha-2-antiplasmin, fibrinogen and other clotting factors will be depleted; this enhances the probability of hemorrhagic complications common after thrombolytic therapy. Fibrolase as isolated from *A.c.contortrix* does not exhibit any detectable plasminogen activator activity. In addition, *A.c.contortrix* fibrolase is free of the significant toxic side effects (such as hemolytic or hemorrhagic properties) associated with the crude venom from which it is derived. Therefore, *A.c.contortrix* fibrolase is being investigated as a promising agent for treatment of myocardial infarction, acute deep-vein thrombosis and pulmonary embolism.

The fibrinolytic enzyme from *A.c.contortrix* has been purified by conventional liquid chromatography methods, by high performance liquid chromatography (HPLC) and by isoelectric focusing, and characterized. This enzyme is a zinc-dependent metalloproteinase (one mole zinc per mole enzyme) with a molecular weight of 23,000. It readily cleaves the $\alpha$- and A$\alpha$-chain of fibrin and fibrinogen, respectively, between $Lys^{413}$-$Leu^{414}$ without activating or degrading plasminogen or Protein C. Accfib has been shown to dissolve aged clots in the renal arteries and iliac veins of rabbits in vivo, and therefore may have significant clinical potential.

A non-hemorrhagic fibrinolytic enzyme, called atroxase, has been isolated from the venom of *Crotalus atrox* [Willis, T. W. and Tu, A. T., *Biochemistry* 27:4769–4777 (1988)]. This enzyme is a zinc-dependent metalloproteinase with a molecular weight similar to that of Accfib. Its in vivo activity has been studied in rats [Willis, T. W. et al., *Thrombos.* Res 53: 19–29 (1989)].

Unfortunately, in addition to its direct fibrinolytic properties, *A.c.contortrix* fibrolase also exhibits a significant degree of general proteolytic activity (as exemplified by azocaseinolytic activity). Thus, in spite of its potential utility in short-term administrations, the properties of the enzyme as a general protease suggest that high dosages or long-term administration thereof might result in the destruction of other systemic proteins through general proteolysis.

It is an object of the present invention to provide novel fibrinolytic agents with peptide bond cleavage specificities which differ from those of the heretofore known fibrinolytic agents, for use as therapeutic agents (for example, in the dissolution of blood clots) and as templates for the development of de novo agents.

It is a further object of the present invention to provide direct fibrinolytic agents with the desirable lack of observable systemic toxicity (as exemplified by the absence of hemorrhagic activity) of *A.c.contortrix* fibrolase but without the degree of proteolytic activity exhibited thereby.

SUMMARY OF THE INVENTION

In accordance with the present invention, there are provided novel fibrinolytic zinc-dependent metalloproteinases exhibiting direct fibrinolytic activity in plasminogen free systems, no detectable plasminogen activation activity in vitro, and no observable systemic toxicity in vivo, as exemplified by the absence of hemorrhagic activity. Several of these enzymes are further characterized by a substantially reduced general proteolytic activity (as measured by azocaseinolytic activity in vitro) relative to *A.c.contortrix* fibrolase, but with maintenance of specific fibrinolytic activity.

BRIEF DESCRIPTION OF THE DRAWINGS

The invention may be better understood with reference to the accompanying drawings, in which:

FIGS. 3(A–H) illustrate elution profiles obtained in determinations of purity of *Crotalus basiliscus basiliscus* venom and components thereof by reverse-phase chromatography;

FIG. 5 illustrates SDS-polyacrylamide gel electrophoresis of the purified fibrinolytic enzymes from *Crotalus basiliscus basiliscus* venoms and various standards;

FIGS. 8(A(1–4) and B(1–4)) illustrate time-course analyses of the effects of fibrinolytic enzymes on fibrinogen and fibrin;

FIGS. 11(A and B) illustrate the results of reverse-phase chromatographic analysis of a Cbfib2 digest of fibrinogen.

DETAILED DESCRIPTION OF THE INVENTION

Figure 1:
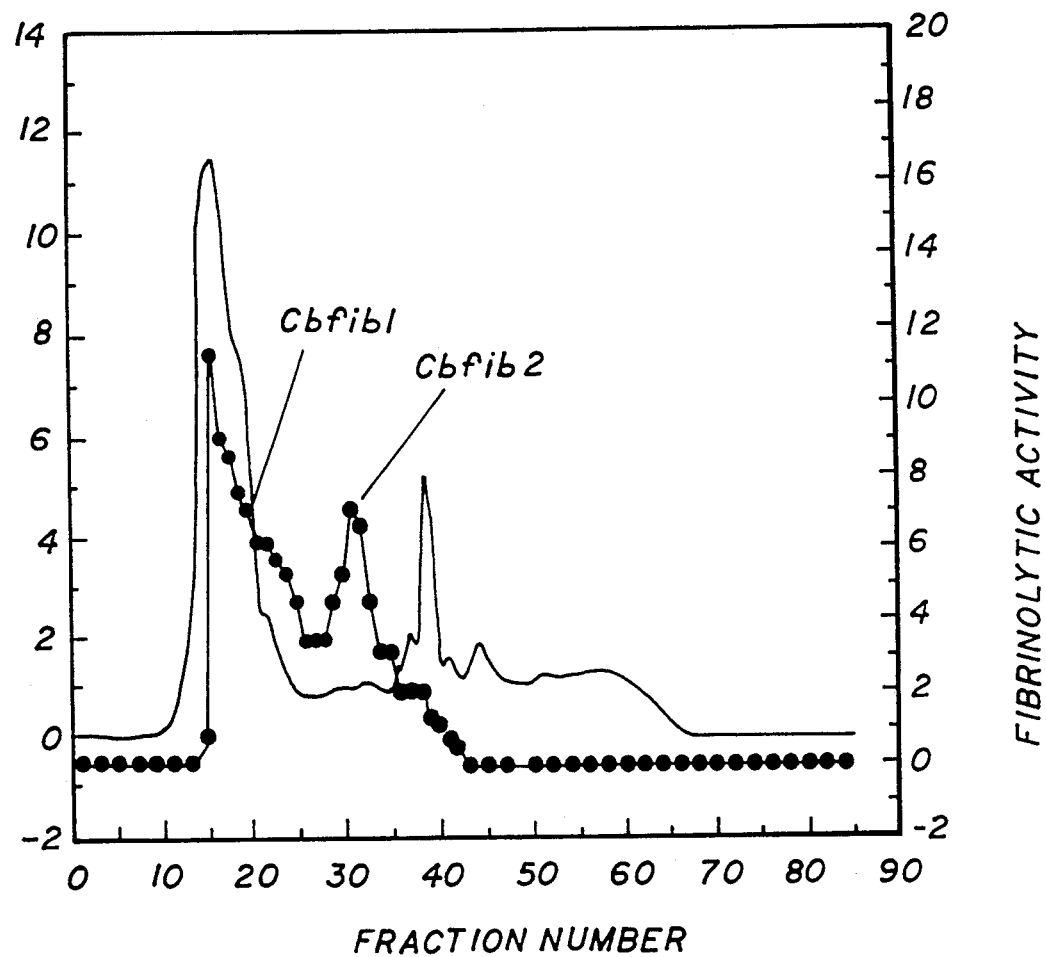
FIG. 1 illustrates the results of hydrophobic interaction chromatography of *Crotalus basiliscus basiliscus* venom.

In accordance with one aspect of the present invention, three distinct fibrinolytic enzymes have been purified from the venom of *Crotalus basiliscus basiliscus* (the Mexican west coast rattlesnake). High-performance liquid chromatography-based purification of the venom was employed, comprising the following steps: (1) hydrophobic interaction chromatography; (2) hydroxylapatite chromatography; and (c) anion exchange chromatography. Following hydrophobic interaction chromatography, two fibrinolytic activity peaks were detected; these were denominated Cbfib1 and Cbfib2. Upon hydroxylapatite chromatography, Cbfib1 was shown to consist of two components, Cbfib1.1 and Cbfib1.2. Both Cbfib1.1 and Cbfib1.2 were purified to homogeneity using anion exchange chromatography. SDS-polyacrylamide gel electrophoresis revealed that Cbfib1.1 and Cbfib1.2 had similar molecular weights (approximately 27,000); Cbfib2 displayed a molecular weight of 25,500. The enzymes do not appear to be glycoproteins.

Tryptic digests of all three enzymes, analyzed by high-performance reverse-phase chromatography, suggest that Cbfib1.1 and Cbfib1.2 are closely related, and different from Cbfib2; the latter displayed more similarity with Cbfib1.2 than with Cbfib1.1. Specific fibrinolytic activity for all three enzymes was very similar, but general proteolytic activity varied substantially with Cbfib2 showing a 12-fold higher specific proteolytic activity when compared to Cbfib1.1 and Cbfib1.2. None of these enzymes exhibited hemorrhagic activity when injected (up to 100 µg) subcutaneously into mice. Cbfib1.1 and Cbfib1.2 action against fibrinogen was directed equally against both the Aα and Bβ-chains. Against fibrin, the rate of degradation of the α-chain was considerably higher than that of the β-chain. Cbfib2 shows mainly α-fibrin(ogen)ase activity, with limited activity on the β-chain. Several fibrinogen cleavage sites on the Aα-chain have been identified: Cbfib1.1 and Cbfib1.2 cleave at $Lys^{413}$-$Leu^{414}$, $Ser^{505}$-$Thr^{506}$ and $Tyr^{560}$-$Ser^{561}$. Cbfib2 cleaves mainly at $Gly^{254}$-$Ser^{255}$ and $Pro^{516}$-$Met^{517}$.

The present invention is based in part upon the determination that the direct fibrinolytic activity of fibrinolytic enzymes similar in activity profile to *A.c.contortrix* fibrolase is not necessarily associated with the level of proteolytic activity exhibited by Accfib. In particular, the determination that fibrinolytic enzymes, for example as isolated from the venom of *Crotalus basiliscus basiliscus*, may exhibit a substantial level of fibrinolytic activity while demonstrating significantly less proteolytic activity (e.g., about 70% of the corresponding proteolytic activity of Accfib) has significant ramifications with respect to the development of improved fibrinolytic agents for therapeutic applications. The novel enzymes may be particularly advantageous, in that the exploitation of the direct fibrinolytic properties of Accfib may be hampered by undesired side-reactions due to its proteolytic properties. For example, in addition to the desired fibrinolysis, administration of Accfib may result in some undesired degradation of other plasma proteins; notwithstanding the substantial improvement relative to plasminogen activators achieved through the use of Accfib, a reduction in general proteolytic activity without a significant loss of direct fibrinolytic activity provides the obvious advantage of even greater selectivity. This enhanced selectivity, in turn, may permit the administration of larger amounts of the inventive metalloproteinases than might be possible if the general proteinolytic activity were found to have adverse consequences on the organism being treated.

Except as indicated herein, the novel fibrinolytic enzymes of the present invention are similar in properties and utility to the metalloproteinases disclosed in U.S. Pat. No. 4,610,879, for example, the fibrolase as isolated from the venom of *A.c.contortrix*. Thus, the enzymes of the present invention are expected to be essentially devoid of toxic side effects in vivo when administered in an amount effective to achieve fibrinolysis. This is exemplified by the lack of any observable hemorrhagic activity when the enzymes are administered in the manner described.

The novel metalloproteinases may be applied therapeutically over a range of concentrations which may readily be determined by routine screening procedures. The fibrinolytic enzymes of the invention (which have levels of fibrinolytic activity roughly comparable to Accfib) may be administered as disclosed in U.S. Pat. No. 4,610,879 in concentrations of from about 0.1 to about 2.0 mg/ml in physiological saline solution, although other appropriate carriers and techniques which are known in the art may be employed depending upon the particular treatment required. Dosages may be adjusted as described in U.S. Pat. No. 4,610,879; however, the reduced general proteinolytic activity of several of the metalloproteinases of the present invention may permit the use of larger dosages than might be appropriate with Accfib without a substantially increased risk of possibly adverse systemic response.

Although the following description of the isolation and characterization of an embodiment of the novel metalloproteinases of the invention relates to the purification of enzymes (Cbfib1.1, Cbfib1.2 and Cbfib2) from the venom of *Crotalus basiliscus basiliscus*, the present invention is not limited to these specific enzymes or to this method of preparation. For example, venoms from other snake species have been shown to actively lyse blood clots; using the techniques disclosed herein and in U.S. Pat. No. 4,610,879, it would be well within the skill of the worker in the field to determine whether these venoms contain one or more direct fibrinolytic agents having the characteristic pI and activity profile of the metalloproteinases of the invention. In addition, while the instant disclosure is directed primarily to discussions of the intact enzymes, it would be readily apparent to a person of ordinary skill in the art that particular fragments of the enzymes may in fact exhibit an activity profile substantially identical to the intact enzyme. Accordingly, the present invention contemplates the use of portions of the native enzymes, as well as of the native enzymes themselves.

Further, the novel enzymes of the present invention or the active portions thereof may also be prepared by exploiting a variety of biochemical methods in current use, such as genetic engineering or the like. Thus, the purified proteins may be partially sequenced (as is reported herein) and the sequence information used to deduce nucleotide sequences for making probes to identify the gene or genes that encodes a given protein. Once identified, the genes may be isolated and cloned into expression vectors. These vectors may be used to transform competent hosts to produce transformants that are capable of producing the snake venom protein.

Sources of DNA sequences encoding for the proteins include isolated DNA from suitable cells or cell lines, cloned DNA from a genomic library or cloned DNA from a messenger RNA library, where the total messenger RNA is reverse transcribed to DNA and cloned. Once a DNA sequence is identified which encodes for a protein of interest, the sequence of bases may be determined by known means, e.g., Maxam and Gilbert, *Proceedings Nat'l Acad. Sci. USA* 74:560 (1977). In addition, hybrid DNA technology may be employed for obtaining expression. The DNA sequence may be restriction mapped and appropriate sites for cleavage defined. In this way, the sequence may be excised and introduced into a vector having the appropriate regulatory signals. Further, the sequence encoding a native protein may then be manipulated (for example, by single or multiple mutations or deletions) in a manner well known in the art to provide modified proteins, in which changes of one or more amino acids have been introduced. Following the procedures described herein, the determination of whether a particular polypeptide exhibits an activity profile characteristic of the inventive metalloproteinases would then be a matter of routine experimentation. Accordingly, the present invention contemplates both the native enzymes and mutations thereof which exhibit the characteristic activity profile defined herein.

The invention will be better understood by reference to the following example which is intended for purposes of illustration and is not to be construed as in any way limiting the scope of the present invention, which is defined in the claims appended hereto.

EXAMPLE

High performance liquid chromatography (HPLC) grade solvents and chemicals were purchased from VWR Scientific, Cerritos, Calif.; HPLC grade trifluoracetic acid was purchased from Pierce, Redford, Tenn. Venoms were obtained from Biotoxins, Inc., St. Cloud, Fla. Plasminogen-free human fibrinogen (Kabi Diagnostica, grade L) was obtained from Helena Laboratories, Beaumont, Tex. Standard human plasmin (2nd International Reference Preparation) was obtained from the National Institute for Biological Standards and Control, London, United Kingdom. Accfib was prepared according to the method described by Retzios and Markland [Retzios, A. D. and Markland, F. S., *Protein Expression and Purification* 1:33-39 (1990)]. N-tosyl-L-phenylalanine chloromethyl ketone $(TPCK)^3$-treated trypsin was obtained from Worthington Biochemical Corporation, Freehold, N.J. Reagents for immunoblotting were purchased from Sigma Chemical Co., St. Louis, Mo. All other reagents were of analytical grade.

Purification of the fibrinolytic enzymes was performed on a Perkin-Elmer 410 Bio HPLC system equipped with the LC-95 variable-wavelength detector and LC-100 integrator. Reverse-phase chromatography for the evaluation of purity of preparations, tryptic digest analysis and isolation of fibrinogen fragments was performed on a Spectra-Physics 8800-HPLC system equipped with Spectra-Physics 8450 variable-wavelength detector. Both systems were connected to the Spectraphysics WINner data acquisition module.

For hydrophobic interaction chromatography, the polypropyl-aspartamide column (21 mm×250 mm) from PolyLC, Columbus, Ohio was employed. Hydroxylapatite chromatography was performed on a SynChropak HAP-5 hydroxylapatite column (21.2 mm×100 mm) from SynChrom, Inc., Lafayette, Ind. Anion-exchange chromatography was performed on a semipreparative SynChropak AX 300 column (10 mm×250 mm) from SynChrom, Inc. Reversephase chromatography for the determination of preparation purity was performed on a $C_4214TP54$ or $C_{18}218TP54$ column (4.1 mm X 250 mm) from Vydac, Hesperia, Calif.

Purification of fibrinolytic enzymes from the venom of *Crotalus basiliscus basiliscus* was accomplished using a three-step HPLC-based chromatographic procedure. The preparative polypropyl-aspartamide column was employed for the first step. The column was equilibrated with buffer A (0.1M sodium phosphate buffer, pH 6.8, containing 1.0M ammonium sulfate and 0.05% $NaN_3$). Venom (1 g dissolved in 12 ml of buffer A) was centrifuged, filtered and added to the column. Elution was then carried out by a linear increase in the concentration of buffer B (0.1M sodium phosphate buffer, pH 6.8, containing 0.05% $NaN_3$). The flow rate was kept constant at 3 ml/min. The following elution protocol was used: (a) after injection of venom, the column was washed with buffer A for 25 minutes; (b) a linear gradient to 100% buffer B was established over 90 minutes; and (c) elution was completed by maintaining 100% buffer B isocratically for 60 minutes.

Fibrinolytic activity pools resulting from hydrophobic interaction HPLC were concentrated by 80% ammonium sulfate precipitation and dialyzed against 0.01M sodium phosphate buffer, pH 6.8. The SynChropak hydroxylapatite HPLC column was equilibrated with 0.01M sodium phosphate buffer, pH 6.8, containing 0.05% $NaN_3$ and 0.3 mM $CaCl_2$ (buffer A). Elution was performed with a linear gradient of buffer B (0.35M sodium phosphate buffer, pH 6.8, containing 0.05% $NaN_3$, 0.3 mM $CaCl_2$). The flow rate was kept constant at 2 ml/minute. The following elution protocol was employed: (a) after addition of the sample, the column was washed with buffer A for 15 minutes; (b) a linear gradient to 60% buffer B was run over 110 minutes; (c) this was followed with a linear gradient to 100% buffer B over 35 minutes; and (d) the run was completed with isocratic elution at 100% buffer B for 35 minutes.

Pooled fibrinolytic fractions after hydroxylapatite HPLC were concentrated by ammonium sulfate precipitation and dialyzed against 0.01M sodium phosphate buffer, pH 6.8. The dialysates were subsequently injected onto the AX-300 column equilibrated with 0.01M sodium phosphate buffer, pH 6.8, containing 0.05% $NaN_3$ (buffer A). Elution was achieved by a linear gradient with buffer B (0.01M sodium phosphate buffer, pH 6.8, containing 1.0M NaCl, 0.05% $NaN_3$). The flow rate was 1 ml/minute. The following elution protocol was employed: (a) after the addition of sample, the column was washed with buffer A for 20 minutes; (b) a linear gradient to 100% buffer B was established over 120 minutes; and (c) this was followed by isocratic elution at 100% buffer B for 25 minutes.

Tryptic digest mapping of the purified materials was carried out as follows. Prior to tryptic digestion, the enzymes were reduced and carboxymethylated. The fibrinolytic enzymes (2.5 mg) were dialyzed against water, freeze-dried and dissolved in 2 ml of 0.2M Tris buffer, pH 8.2, containing 8M urea. Dithiothreitol (1 mg) was added to each solution (3.2 mM DTT final concentration) and the mixtures were incubated at 37° C. for 1 hour. Iodoacetamide (2 mg) was then added to each tube (5.4 mM iodoacetamide final concentration); the tubes were sealed under oxygen-free nitrogen and incubated in the dark for 1 hour at room temperature. Iodoacetamide treatment was repeated to insure completeness of the reaction. Following reduction and carboxymethylation, the reduced and carboxymethylated enzymes were dialyzed against water and freeze-dried. The carboxymethylated enzymes were dissolved in 1 ml of 0.2M Tris buffer, pH 8.7, containing 2M urea. TPCK-treated trypsin was added at a ratio of 1/40 (w/w, trypsin:fibrinolytic enzyme). Digestion was allowed to proceed at room temperature, with continuous stirring, for 24 hours. Following digestion, the tryptic peptides were separated by reverse-phase chromatography. Each digest (100 $\mu$l) was added to a Vydac $C_{18}$ column and digestion products were eluted using the following protocol: (a) 5 minutes isocratically at 90% solvent A (0.1% TFA in water, 10% solvent B (0.1% TFA in 80% acetonitrile); (b) 80 minutes linear gradient to 65% solvent B.

SDS-polyacrylamide gel electrophoresis (SDS-PAGE) of the enzymes was carried out according to the method of Laemmli [Laemmli, U.K., Nature 227:680-685 (1970)]. Standards used for molecular weight determination were obtained from BioRad and included phosphorylase b (97.4 kDa), bovine serum albumin (66.2 kDa), ovalbumin (45 kDa), carbonic anhydrase (31 kDa), soybean trypsin inhibitor (21.5 kDa) and lysozyme (14.4 kDa).

Isoelectric focusing of the enzymes was carried out using a Bio-Rad mini IEF gel apparatus, Model 111, attached to an Ortec 4100 constant power supply. Bio-Rad ampholyte solutions were used for the determination of the isoelectric points (pI) of the purified proteins. IEF Standard proteins of known pI were obtained from Bio-Rad. Staining was effected with Coomasie blue R-250 and crocein scarlet.

Carbohydrate was determined by the periodic acid-silver staining procedure after SDS-PAGE as described by Dubray et al. [Dubray, G. and Bezard, G., Anal. Biochem. 119:325-329 (1982)]. The detectable amount of carbohydrate using this procedure as carried out herein was 0.28 g using horseradish peroxidase (containing 18% carbohydrate) as a positive control.

Amino acid compositions of the reduced-carboxymethylated proteins were obtained by the method described in Bidlingmeyer et al. [Bidlingmeyer, B. A. et al., J. Chromatogr. 336:93-104 (1984)]. Analyses were performed on the protein samples hydrolyzed in the vapor of constant boiling HCl containing 1% v/v phenol for 24 hours, in vacuo, at 110° C. Phenylthiocarbamyl-amino acids were separated by reverse-phase HPLC using a Nova-Pak $C_{18}$ reverse phase column.

Proteolytic activity was assessed by azocasein hydrolysis. Azocasein was synthesized from alpha-casein and diazotized sulfanilamide as described by Charney and Tomarelli [Charney, J. and Tomarelli, R. M., J. Biol. Chem. 171:501-505 (1947)]. The resulting azocasein solution in 1% sodium bicarbonate had a concentration of 42 mg/ml. To measure proteolytic activity, 0.75 ml of the azocasein solution was added to a 1.5 ml microcentrifuge tube. The test solution containing fibrinolytic enzyme (50 $\mu$l) was added and the tube was incubated at 37° C. for 30 minutes. The reaction was stopped by addition of 0.75 ml of 1.16M perchloric acid and the resulting precipitate removed by centrifugation. Hydrolysis of azocasein was measured as increased absorbance at 390 nm in the supernatant, using as reference azocasein treated in an identical manner but without enzyme. To accurately estimate specific activity (absorbance units 390 nm/mg enzyme), varying quantities of the enzymes were added in order to construct a response curve. The linear part of the curve was used for the estimation of specific proteolytic activity.

Fibrinolytic activity was measured with the fibrin-plate-clearance assay [Bajwa, S. S., Markland F. S. and Russell, F. E., Toxicon 18:285-290 (1980)]. For the preparation of fibrin plates, two buffers are necessary: fibrinogen buffer and gelatin buffer. Fibrinogen buffer is prepared by adding the following: 20.62 g of sodium barbital, 100 ml of 0.1M HCl, 100 ml of "salt solution" (4.89 g $CaCl_2.2H_2O$, 2.79 g $MgCl_2.6H_2O$, 109.12 g NaCl, and $H_2O$ to a total volume of 1 liter), and 1350 ml of $H_2O$. The pH of the buffer is adjusted to 7.75 with concentrated HCl and the volume is adjusted to 2 liters with $H_2O$. The gelatin buffer is prepared as follows: 5.85 g NaCl, 10.31 g sodium barbital, 200 ml of 0.1N HCl, 25 g gelatin and 725 ml of $H_2O$. After preparation of the buffers, the following solutions are made: (a) 32 mg fibrinogen (76.2 mg dry weight of KABI plasminogen-free fibrinogen) is dissolved in 5.25 ml of fibrinogen buffer and 0.75 ml of $H_2O$; (b) 20 $\mu$l of 1000 Units/ml bovine thrombin (USP Thrombostat, Parke-Davis, Morris Plains, N.J.) is added to 0.5 ml of gelatin buffer. Fibrin plates are prepared in disposable Petri dishes (100 × 15 mm) by adding to each plate 6 ml of fibrinogen solution and 200 $\mu$l of thrombin solution. The plates are incubated for 2-3 hours at 37° C. and eight equidistant wells are punched around the circumference of each plate approximately 1 cm from the edge of the plate. Test sample is then added (10 $\mu$l per well) and the plates are incubated for 18 hours at 37° C. To measure areas of lysis accurately, the plates are flooded with 10% TCA solution at the end of the incubation period. The diameters of the lysis areas are then measured against a dark background. As with the proteolytic assay, several enzyme dilutions were tested in order to construct a response curve. A standard response curve is constructed using a solution of reference plasmin (0.5 Plasmin International Units (P.I.U.)/ml) in 0.1M Tris, pH 7.8, containing 0.05M NaCl, and fibrinolytic activity is expressed in P.I.U.

Hemorrhagic activity of the purified fibrinolytic enzymes was evaluated by a modification of the skin test procedure of Kondo et al. [Kondo, H. et al., Jpn. J. Med. Sci. Biol. 13:43-51 (1960)]. In this method, purified enzyme (50-100 $\mu$g) is injected subdermally under the clean shaven backs of white mice (approximately 20 g in weight). After 18 hours, the animals are sacrificed, the skin is removed and the area of hemorrhage on the underside of the skin is measured.

To determine the effect of EDTA on enzyme activity, 50 $\mu$l of 97.5 $\mu$M Cbfib1.1 or 94.2 $\mu$M Cbfib2 were added to separate reaction tubes. Buffer (0.1M Tris, 0.05M NaCl, pH 8.4) containing EDTA was added to a final volume of 0.5 ml such that the molar ratio of EDTA to enzyme was approximately 200, 400, 1000 and 5000. The resulting solutions were stirred continuously at room temperature for 30 minutes and aliquots were removed for azocasein assay at 5 minute intervals. The effects of Zincov [2-(N-hydroxycarboxamido)-4-methylpentanoyl-L-alanyl-glycine amide] on the enzymes was analyzed using a modification of the azocasein assay. A stock solution of 16.5 mM Zincov in azocasein solution (50 mg/ml) was prepared, and several Zincov concentrations were obtained by diluting the stock solution with azocasein. Azocasein solution (0.75 ml) containing 16.5 mM, 8.25 mM, 4.12 mM, 2.06 mM, 1.03 mM or 0 mM Zincov was added to microcentrifuge tubes and warmed to 37° C. The enzyme (50 μl of 45.9 μM Cbfib1.1 or 41 μM Cbfib2) was then added. The enzymes had been preincubated with Zincov, at the concentrations noted above, at room temperature for 15 minutes. After addition of enzyme, the azocasein solution was incubated at 37° C. for 30 minutes and the reaction was stopped by the addition of 0.75 ml of 1.16 mM perchloric acid. Activity was estimated by measuring absorbance at 390 nm (as discussed in connection with the assay for proteolytic activity).

To study the effect of phenylmethylsulfonyl fluoride (PMSF), 10 μl (150 mM in ethanol) was added to 440 μl of 0.1M Tris buffer, pH 8.4, containing 0.05M NaCl and Cbfib1.1 (50 μl of 45.9 μM solution) was quickly added. The resulting solution was incubated at room temperature with continuous stirring for 30 minutes and activity was assayed every 5 minutes using the azocasein assay. The experiment was repeated with Cbfib2 (50 μl or 41 μM solution). The effect of soybean trypsin inhibitor (SBTI) on enzyme activity was also investigated. Cbfib1.1 (50 μl of 9.2 μM solution) was added to 0.95 ml of 0.25 mg/ml SBTI in 0.1M Tris buffer, pH 8.4, containing 0.05M NaCl. The resulting solution was incubated at room temperature with continuous stirring for 30 minutes. Activity was assayed every 5 minutes with the azocasein assay. The experiment was repeated with Cbfib2 (50 μl of 8.2 μM solution).

Fibrinogen (500 μl of 3.8 μM solution in 0.1M phosphate buffer, pH 7.0, containing 0.15M NaCl and 50 mM benzamidine) was pipetted into each of seven 1.5 ml microcentrifuge tubes. Cbfib1.1 (8.5 μl of 4.6 μM solution) was added to each tube to achieve a molar ratio of fibrinogen/enzyme of approximately 50. The resulting solution was incubated at 37° C. At various time points (0 minutes–120 minutes) the reaction in a selected tube was stopped by the addition of 250 μl of 250 mM EDTA solution followed by 500 μl of SDS-PAGE sample buffer. Aliquots were analyzed by SDS-polyacrylamide gel electrophoresis to determine the time sequence of fibrinogen chain cleavage. The experiment was repeated using: Cbfib1.2 (6.6 μl of 5.8 μM enzyme solution) and 0.5 ml of 3.8 μM fibrinogen solution; Cbfib2 (11 μof 3.5 μM solution); and Accfib (16 μl of 2.6 μM solution). In all cases, the molar ratio of fibrinogen/enzyme was approximately 50. To determine the sequence of peptide bond cleavage events during the early stages of incubation, the experiments with Cbfib1.1 and Cbfib2 were repeated with time points ranging from 0 minutes to 5 minutes.

Fibrin was formed from plasminogen-free fibrinogen using the following procedure. 500 μl of 3.8 μM fibrinogen solution in 0.1M Tris buffer, 0.05M NaCl, pH 8.3, was added to each of seven 1.5 ml microcentrifuge tubes. Topical thrombin (5 μl of 1000 U/ml) and 50 μl of 100 mM $CaCl_2$ were also added and the resulting solution incubated at 37° C. for 10 minutes. Following incubation, the resulting fibrin clot was washed thrice by the addition of 0.75 ml of 0.1M sodium phosphate buffer, pH 7.0, containing 0.15M NaCl and 50 mM benzamidine. Subsequently, 0.5 ml of the same buffer was added, followed by the addition of Cbfib1.1 (8.5 μl of 4.6 μM solution) to achieve a molar ratio of fibrin-/enzyme of 50. The resulting solution was incubated at 37° C. At various time points (0 to 24 hours) the reaction in a selected tube was stopped by the addition of 250 μl of 250 mM EDTA solution followed by 500 μl of SDS-PAGE sample buffer. Aliquots were analyzed by SDS-polyacrylamide gel electrophoresis to determine the time sequence of fibrin degradation. The experiment was repeated for: Cbfib1.2 (where 6.6 μl of 5.8 μM solution was added to each tube containing 0.5 ml of fibrin solution); Cbfib2 (11 μl of 3.5 μM solution); and Accfib (16 μl of 2.6 μM solution). In all cases, the molar ratio of fibrin/enzyme was approximately 50.

Determination of cleavage sites was effected as follows. Fibrinogen (30 nmoles) was dissolved in 2 ml of 0.1 Tris buffer, pH 8.0, containing 50 mM benzamidine and 0.02% sodium azide. To this solution 13.5 μl of Cbfib1.1 (0.6 nmol) was added. The solution was incubated at 37° C. for 1 minute and the reaction was stopped by the addition of 1 ml of 250 mM EDTA. The experiment was repeated with an incubation time of 5 minutes. The solutions were then brought to 8M urea and degraded fibrinogen was reduced and carboxymethylated. Reductive carboxymethylation was performed by the addition of dithiothreitol in a 10-fold molar excess over fibrinogen. After passing oxygen-free nitrogen through the solution, it was incubated at room temperature for one hour. Iodoacetamide was then added in a 10-fold molar excess over fibrinogen, and alkylation was allowed to proceed in the dark at room temperature for one hour under oxygen-free nitrogen. For Cbfib2, the same fibrinogen solution was prepared and 17.6 μl of Cbfib2 (0.6 nmol) was added to obtain a fibrinogen to Cbfib2 ratio of approximately 50. The solution was incubated at 37° C. for 2 minutes and the reaction was stopped by the addition of 1 ml of 250 mM EDTA. The experiment was then repeated with an incubation time of 5 minutes as for Cbfib1.1. The solutions were brought to 8M urea and the proteolytically degraded fibrinogen was reduced and carboxymethylated as described above. Fibrinogen fragments were separated by reverse-phase HPLC on a Vydac $C_4$ column. The isolated peptides were further purified by reverse phase chromatography on a Vydac $C_{18}$ column and the amino-terminal amino acid sequences (6–8 residues) were determined by automated gas-phase sequencing.

Following hydrophobic interaction chromatography of crude venom, examination of the elution fractions using the fibrin-plate assay revealed two main activity peaks, named Cbfib1 and Cbfib2 (FIG. 1). In FIG. 1, the solid line indicates effluent absorbance at 280 nm; the other line indicates fibrinolytic activity (expressed in $cm^2$ of fibrin plate cleared per 10 μl of fraction tested).

Figure 2:
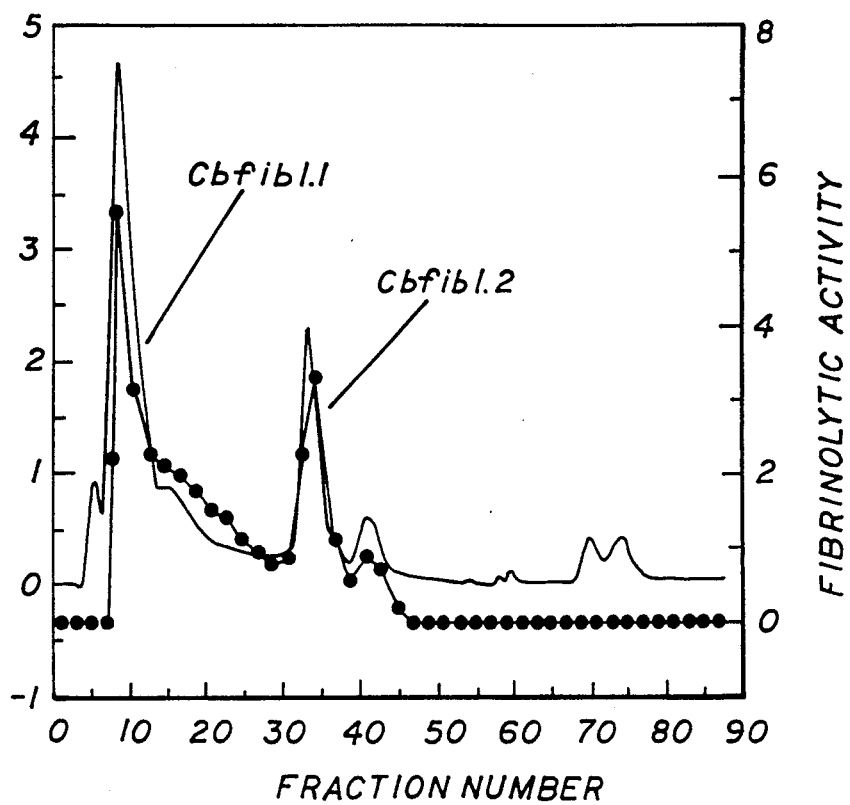
FIGS. 2(1 and 2) illustrate the results of hydroxylapatite chromatography of fibrinolytic activity pools resulting from hydrophobic interaction chromatography.
Figure 2:
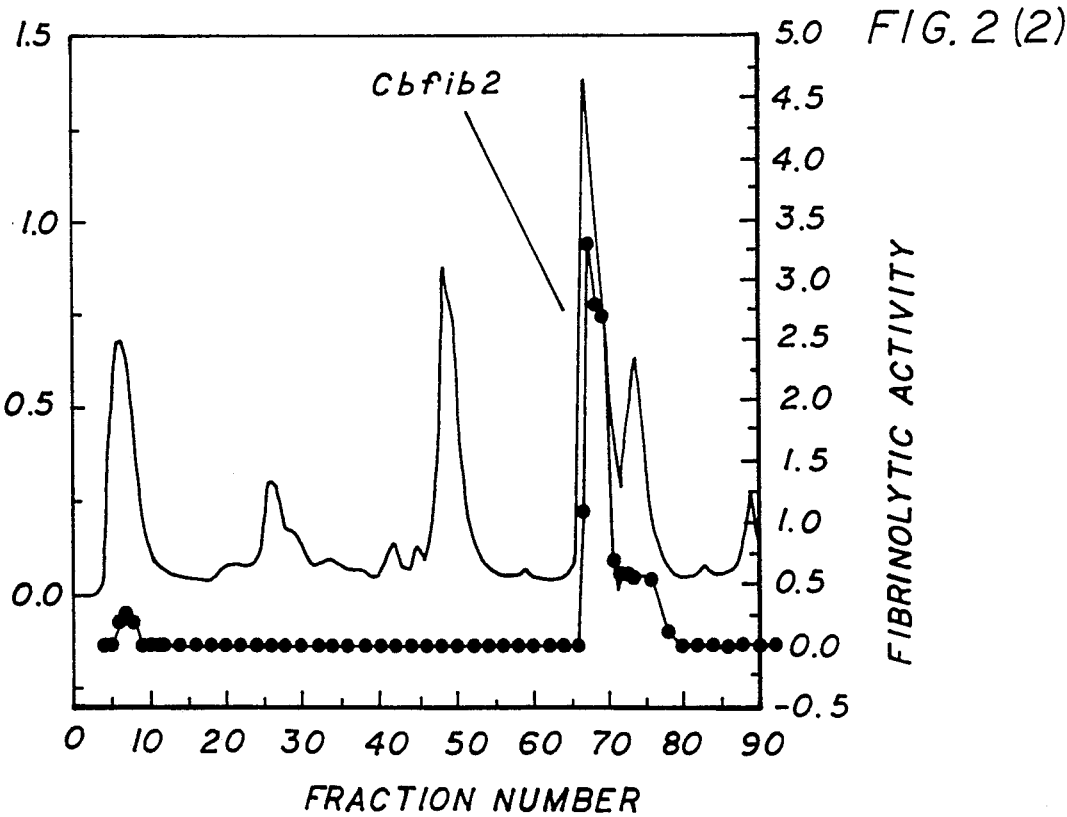

The two peaks were pooled separately and were further fractionated by hydroxylapatite chromatography. The fibrinolytic activity profile of Cbfib1 showed two main activity peaks Cbfib1.1 and Cbfib1.2 (FIG. 2(1). The elution profile of Cbfib2 revealed a single activity peak (FIG. 2(2)). As in FIG. 1, the solid line in FIG. 2 indicates effluent absorbance at 280 nm, whereas the other line indicates fibrinolytic activity.

SDS-PAGE and reverse-phase (RP-) HPLC indicated that Cbfib1.1 and Cbfib1.2 contained a number of contaminants after hydroxylapatite HPLC (FIGS. 3(A–H)). Aliquots from each purification step (50–100 μl) were injected into a Vydac $C_4$ RP-HPLC column. The components were separated by the following elution protocol: 0–5 minutes isocratic elution with 90% solvent A (0.1% TFA in $H_2O$)-10% solvent B (0.1% TFA in 80% acetonitrile, 20% $H_2O$); 55 minutes linear gradient to 80% solvent B. A flow rate of 1 ml/minute was employed. The following elution profiles are shown: (FIG. 3A) crude venom; (FIG. 3B) Cbfib1 after hydrophobic interaction chromatography; (FIG. 3C) Cbfib2 after hydrophobic interaction chromatography; (FIG. 3D) Cbfib1.1 after hydroxylapatite chromatography; (FIG. 3E) Cbfib1.2 after hydroxylapatite chromatography; (FIG. 3F) Cbfib2 after hydroxylapatite chromatography; (FIG. 3G) Cbfib1.1 after anion exchange chromatography; and (FIG. 3H) Cbfib1.2 after anion exchange chromatography. Both enzymes appeared homogeneous by reverse-phase HPLC after anion exchange chromatography; similarly, Cbfib2 appeared homogeneous after hydroxylapatite HPLC.

Figure 4:
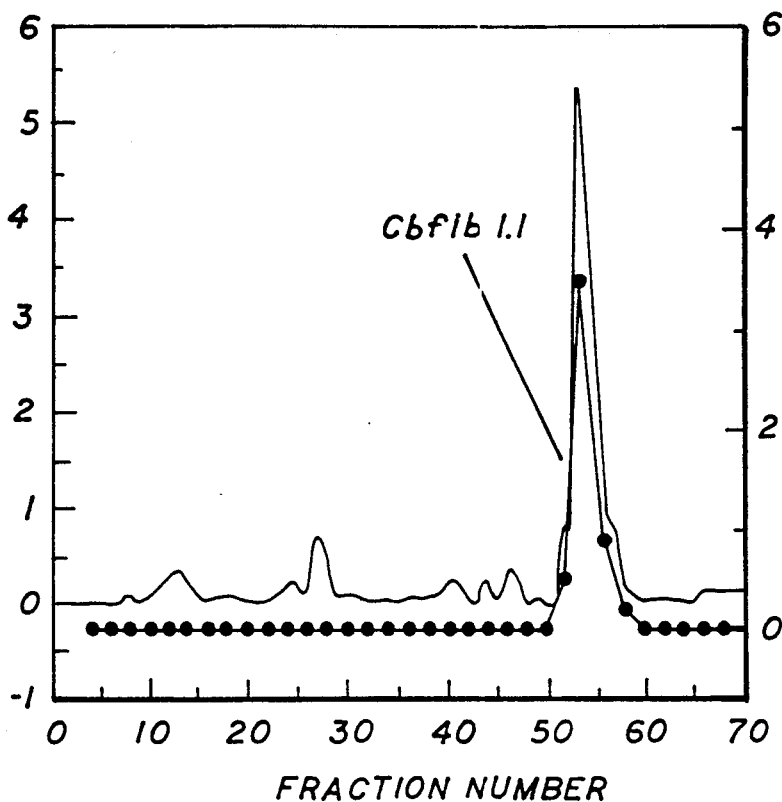
FIGS. 4(1 and 2) illustrate the results of anion-exchange chromatography for final purification of fibrinolytic components resulting from hydroxylapatite purification of Cbfib1.1 and Cbfib1.2.
Figure 4:
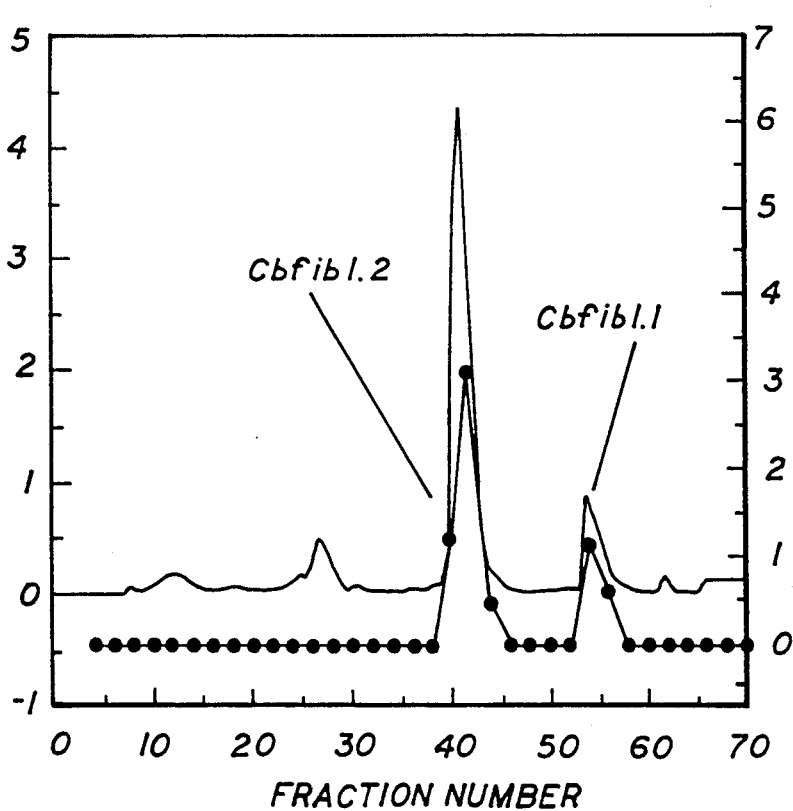

The Cbfib1.1 and Cbfib1.2 fractions were further purified by anion-exchange chromatography (FIGS. 4(1 and 2)). As in FIG. 1, the solid line indicates effluent absorbance at 280 nm, while the other line indicates the fibrinolytic activity of the resulting fractions.

Table 1 summarizes the purification procedure for the three enzymes. The recovery for each enzyme is quite low since they were purified separately. However, total recovery of activity for the three enzymes is over 50%. It should be noted that these three enzymes comprise a significant portion of the total venom protein, approximately 30%, with the major component being Cbfib1.1.

Figure 5:
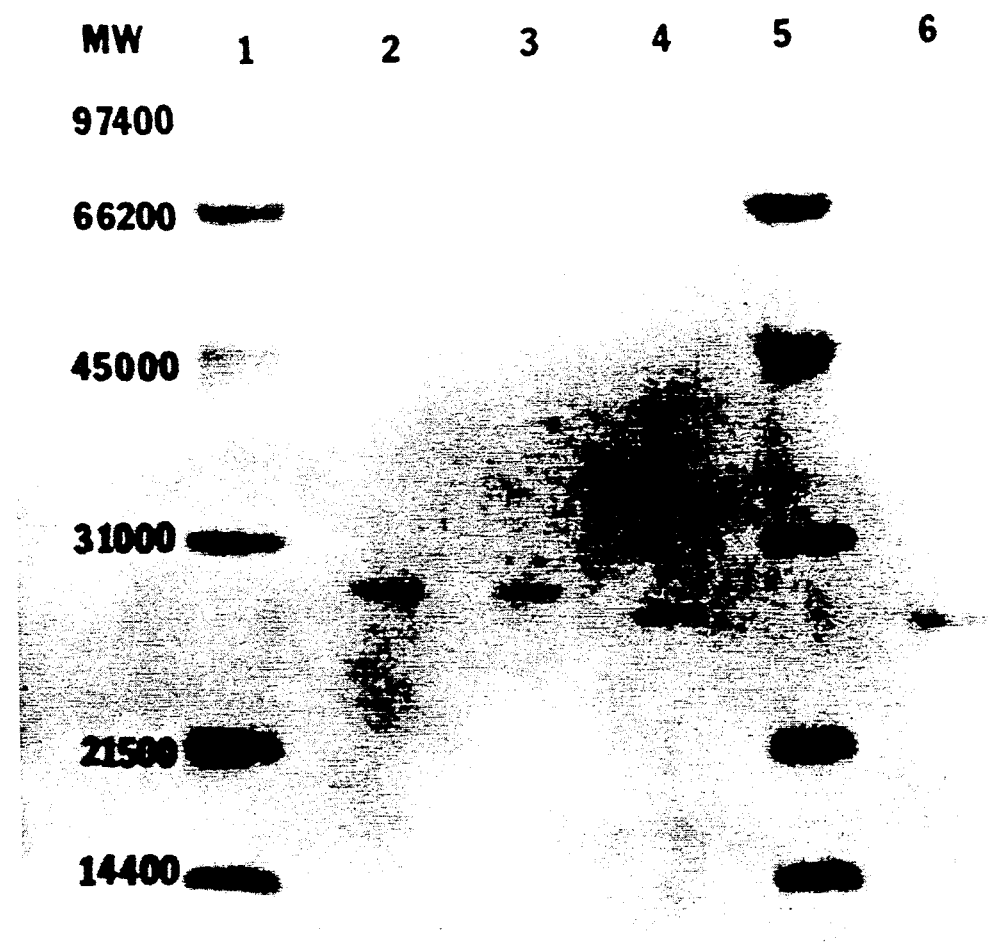

SDS-PAGE of the purified enzymes (FIG. 5) reveals that the molecular weights of Cbfib1.1 and Cbfib1.2 are approximately 27,000; the molecular weight of Cbfib2 is slightly lower at 25,500. In FIG. 5, the lanes contain: (1) SDS-PAGE standards; (2) Cbfib1.1; (3) Cbfib1.2; (4) Cbfib2; (5) SDS-PAGE standards; and (6) Accfib. Isoelectric focusing revealed that both Cbfib1.1 and Cbfib1.2 have low isoelectric points at pH 4.1 and 4.7, respectively. By comparison, Cbfib2 possessed a considerably higher isoelectric point at pH 8.5. The difference in isoelectric points between the enzymes suggests that the dissimilarities observed in molecular weights could be due to the influence of intrinsic charge differences on mobilities in SDS-PAGE.

The amino acid compositions of the enzymes are presented in Table II; the results are the average of two 24 hour hydrolyses for each enzyme. The number of residues has been estimated at approximately 211 in each enzyme. There is extensive similarity between Cbfib1.1 and Cbfib1.2 except for the number of valine residues. Cbfib2 appears similar to the other two enzymes except for an increased number of lysine and alanine residues. The fibrinolytic enzymes contain little or no carbohydrate as revealed by periodic acid-silver staining [Dubray, G. and Bezard, G., Anal. Biochem. 119:325-329 (1982)]. Based on sensitivity of this procedure and the large amount of fibrinolytic enzymes applied to SDS-PAGE (30-50 µg), the content of carbohydrate, if present, must be less than 1%.

Cbfib1.1 and Cbfib1.2 are fully inactivated within 5 minutes by incubation with 5000-fold molar excess EDTA. At 200- to 100-fold molar excess, activity loss varies from 20 to 75%. Cbfib1.1 and Cbfib1.2 do not lose activity upon incubation with serine protease inhibitors including SBTI (equal molar ratio) and PMSF (3.0 mM). Cbfib2 is fully inactivated within 5 minutes by incubation with 1000-fold molar excess EDTA and although not affected by an equal molar ratio of SBTI, it is inhibited approximately 15% when treated with 3.0 mM PMSF. With Zincov, inhibition studies produced similar results for Cbfib1.1 and Cbfib2. When the enzymes were preincubated with the inhibitor and assayed in the presence of the inhibitor, 5% of azocaseinolytic activity remained at 16.5 mM Zincov concentration, 8% at 4.1 mM and 12% at 1.0 mM. Without preincubation of the enzymes with Zincov, inhibition was considerably weaker. This, 80% of the original activity remained at 4.1 mM Zincov concentration. Similar weak competitive inhibition by Zincov has been observed for Accfib ($K_i=16$ mM), an enzyme whose zinc content has been directly measured by zinc metal analysis. These findings suggest that the C. b. basiliscus enzymes are also zinc-dependent and functionally similar to Accfib.

Figure 6:
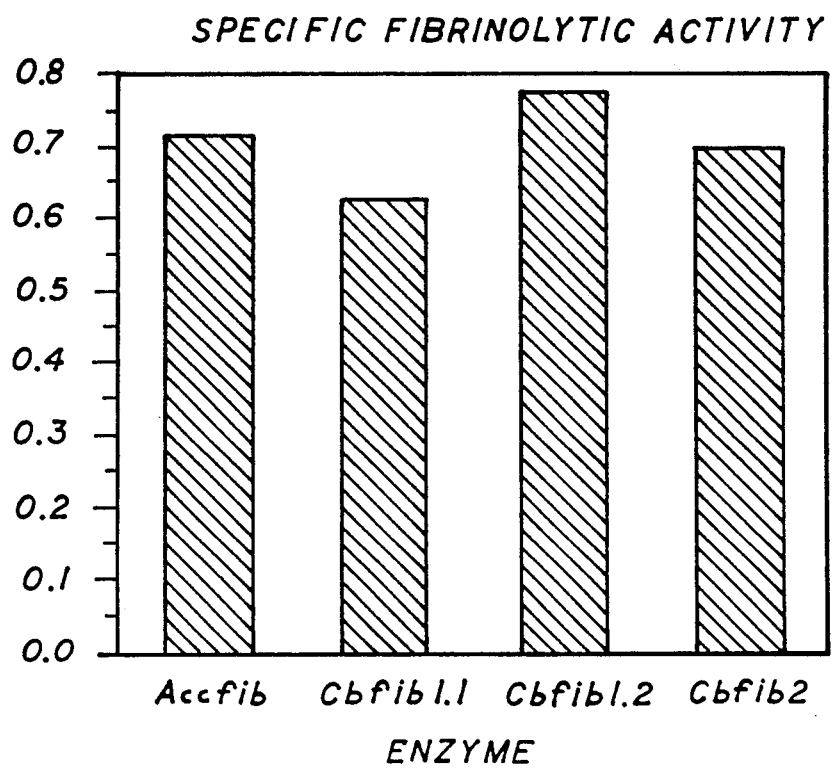
FIGS. 6(1 and 2) are a comparison of functional properties of *Crotalus basiliscus basiliscus* fibrinolytic enzymes.
Figure 6:
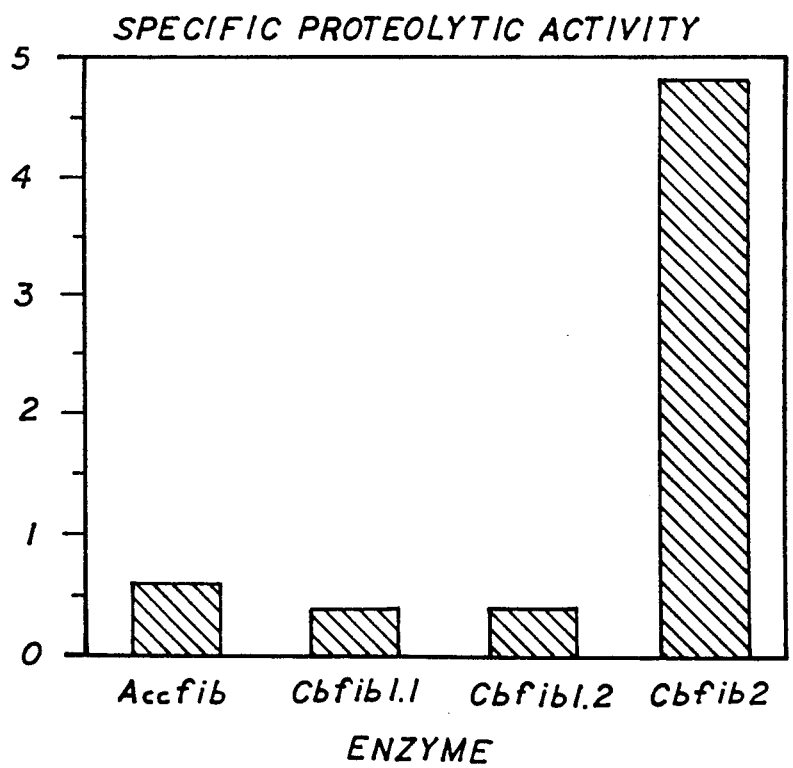

Specific fibrinolytic activities for Cbfib1.1, Cbfib1.2 and Cbfib2 were measured and compared to that of Accfib (FIG. 6(1)). The differences were minor with specific activities ranging around 0.7 PIU/mg protein. However, general proteolytic activities (using azocasein as a substrate) showed wide divergence (FIG. 6(2)). The specific azocaseinolytic activity of Cbfib2 is 7.9-fold higher than the corresponding activity of Accfib and 12-fold higher than Cbfib1.1 and Cbfib1.2. The specific azocaseinolytic activity of Cbfib1.1 and Cbfib1.2 is approximately 70% of that of Accfib. Using the skin hemorrhagic assay, modified from that previously described by Kondo et al., none of the fibrinolytic enzymes exhibited hemorrhagic activity as evidenced by a lack of extravascular bleeding on the underside of the mouse skin.

Figure 7A:
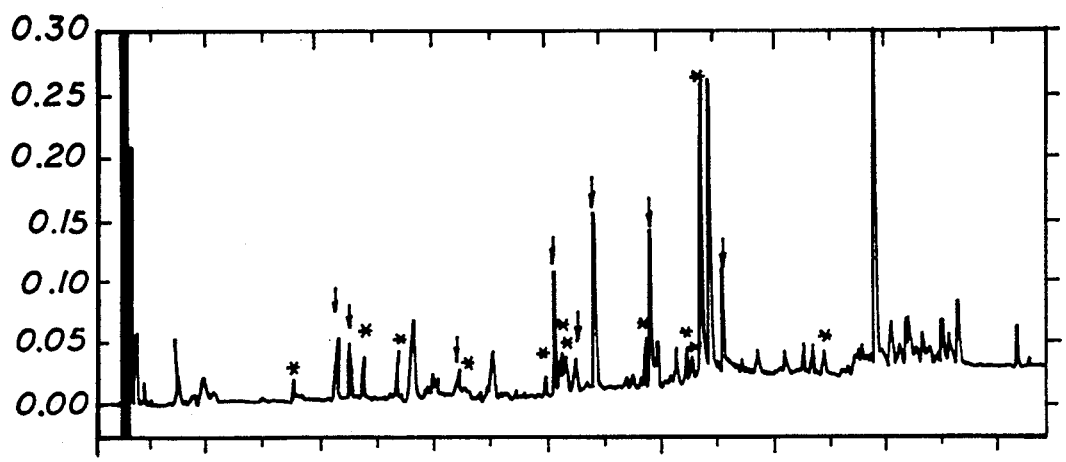
FIGS. 7(A–C) illustrate the results of reverse-phase chromatographic analysis of tryptic digests of reduced-carboxymethylated *Crotalus basiliscus basiliscus* fibrinolytic enzymes.
Figure 7B:
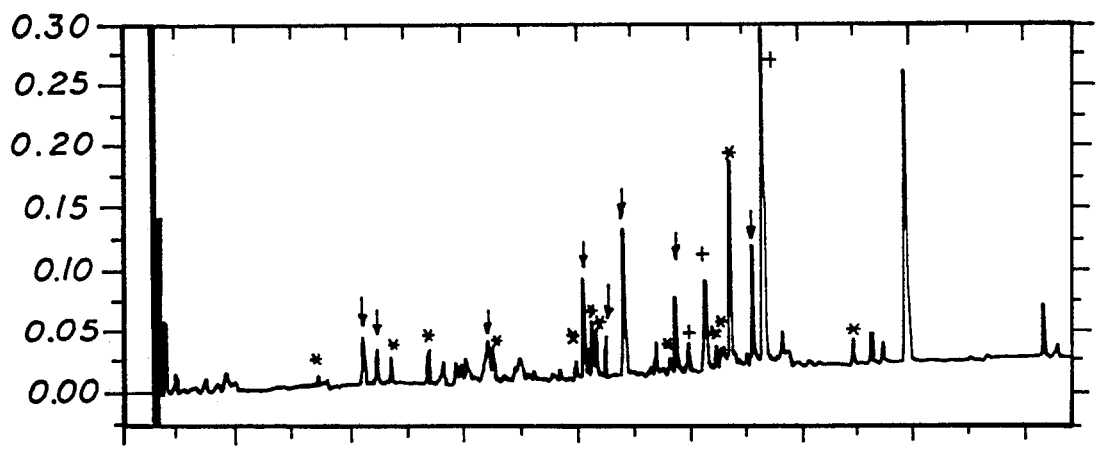
Figure 7C:
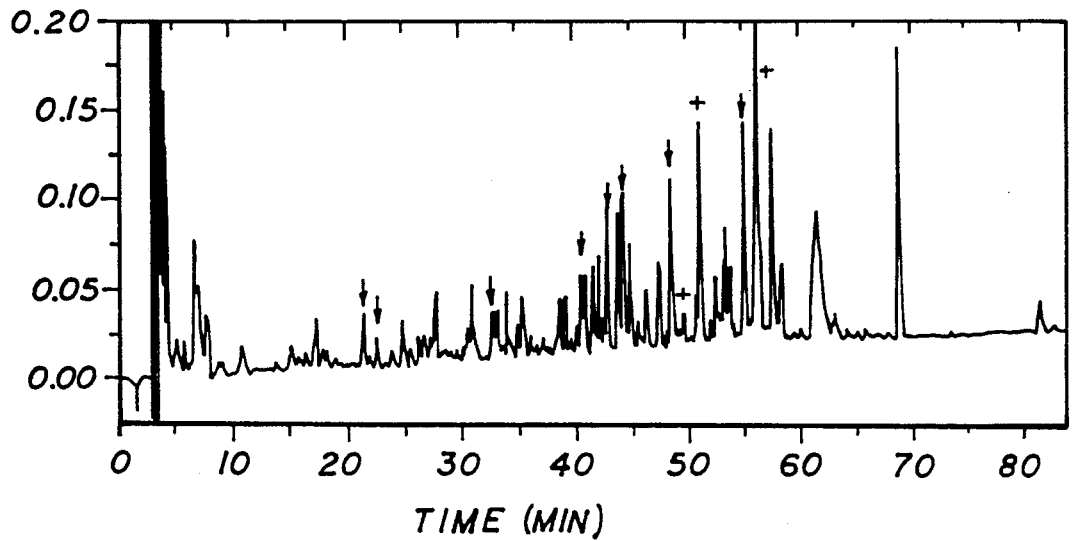

Comparison of tryptic digestion profiles of the C.b.basiliscus fibrinolytic enzymes by $C_{18}$ reverse phase HPLC revealed, as other results already suggested, a significant degree of similarity between Cbfib1.1 and Cbfib1.2 (FIGS. 7(A-C)). In FIG. 7, arrows indicate peptides eluting with similar retention times in all three digests; asterisks indicate peptides that elute in similar positions only for Cbfib1.1 and Cbfib1.2; and crosses indicate peptides that elute in similar positions only for Cbfib1.2 and Cbfib2. The differences in tryptic peptide elution patterns between Cbfib1.1 and Cbfib1.2 are numerous enough not to be accounted for by a single amino acid substitution. Cbfib2 exhibits extensive differences with Cbfib1.1 and Cbfib1.2. The three HPLC elution profiles revealed between 25-35 peptide peaks in each. This is fairly consistent with the lysine and arginine content of the enzymes, which varies between 22 to 24 residues. There appears to be 10 peptides that elute in identical positions for all three enzymes, 12 that elute in identical positions when comparing Cbfib1.1 and Cbfib1.2, and 3 peptides that have similar retention times when comparing Cbfib1.2 to Cbfib2. These results suggest that Cbfib2 is more closely related to Cbfib1.2 than to Cbfib1.1, but that all three have most likely evolved from some common precursor.

All three Crotalus basiliscus enzymes degrade fibrin and fibrinogen, and they apparently degrade these proteins by cleavage of peptide bonds different than those cleaved by Accfib, a venom enzyme previously investigated for specific cleavage sites in fibrinogen [Retzios, A. D. and Markland, F. S., Thrombos. Res. 52:541-552 (1988)]. The number of fibrin/fibrinogen cleavage products observed and the mode of action is identical for Cbfib1.1 and Cbfib1.2, indicating that these enzymes are functionally very similar, as well as being structurally related. However, Cbfib2 displays a fibrin/fibrinogen degradation profile that is substantially different from that of Cbfib1.1 and Cbfib1.2.

Figure 8B:
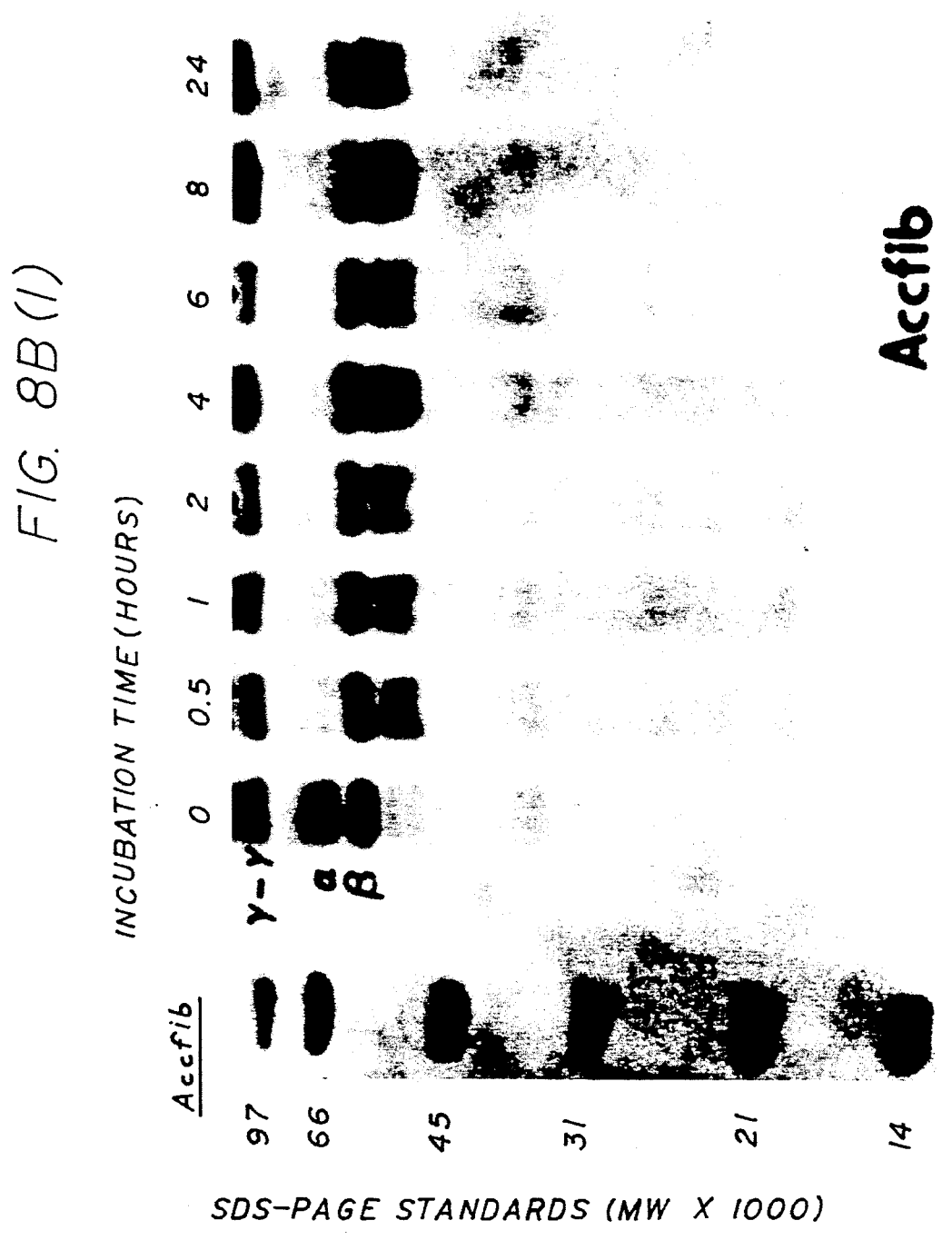

FIGS. 8A(1-4) and B(1-4) reveal that overall pattern of fibrinogen and fibrin degradation and indicates the differences between the cleavage patterns of the four fibrinolytic enzymes under study. FIGS. 8A(1-4) illustrate the time-course analysis by SDS-PAGE (10% acrylamide gels) of fibrinogen digestion; FIGS. 8B(1-4) illustrate the time-course analysis by SDS-PAGE (10% acrylamide - 8M urea gels) of fibrin digestions. It is immediately evident that whereas Accfib makes a single initial cleavage on the Aα-chain and degrades the Bβ-chain much more slowly, Cbfib1.1 and Cbfib1.2 catalyze a number of cleavages and degrade the Bβ-chain much faster than Accfib. In contrast Cbfib2 degrades the Bβ-chain even more slowly than Accfib and it cleaves the Aα-chain at several positions which are different than those cleaved by Cbfib1.1 and Cbfib1.2. None of these enzymes appear to degrade the γ-chain. The degradation of fibrin by the four enzymes produces similar SDS-PAGE profiles when compared to those produced following degradation of fibrinogen, although the digestion times are longer with fibrin. In all cases the γ—γ dimer remains intact during the course of digestion (fibrin was only cross-linked to the level of γ—γ dimer formation).

Figure 9A:
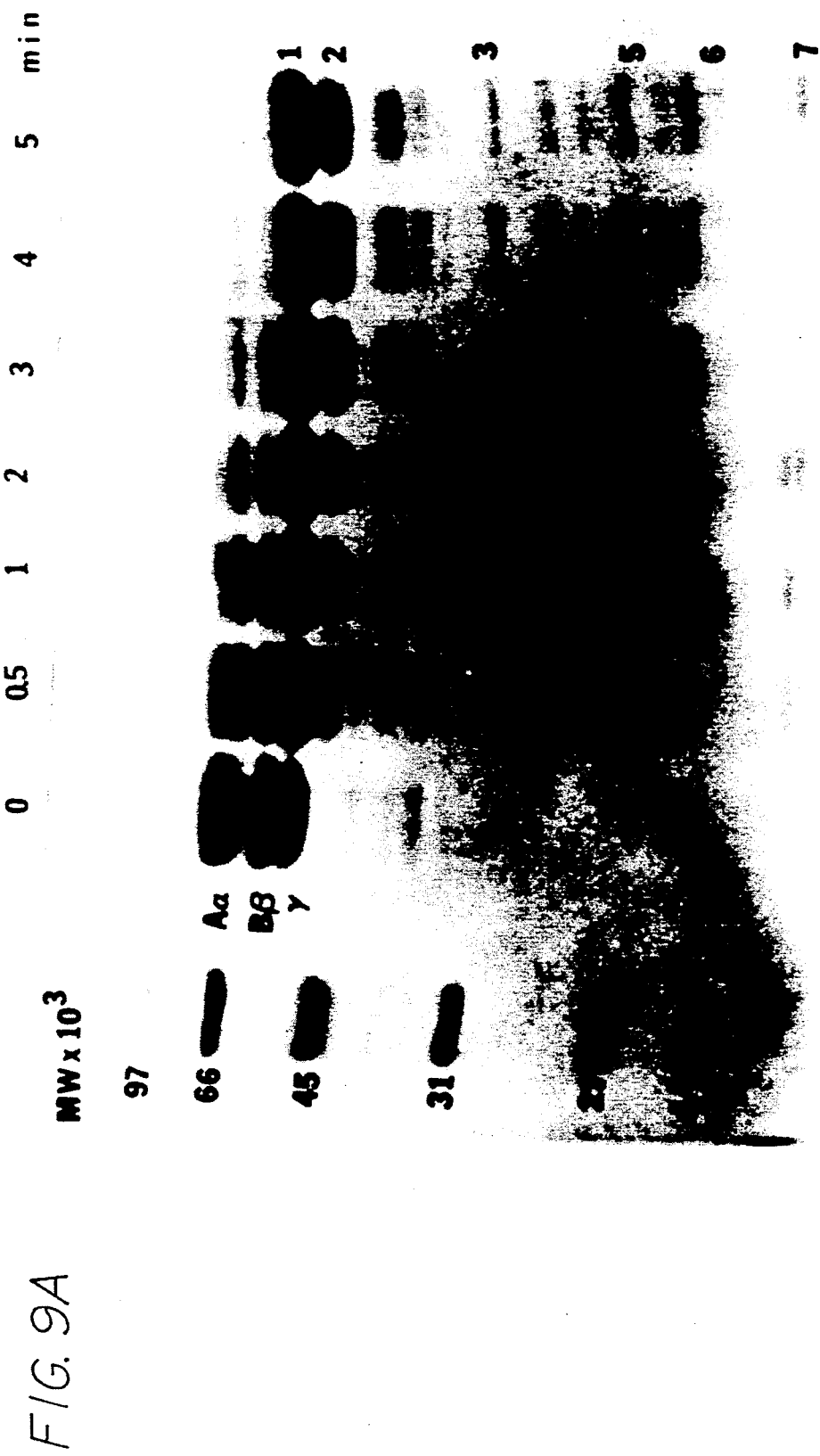
FIGS. 9(A–B) illustrate time-course analyses of fibrinogen degradation events in the early stages of digestion using Cbfib1.1 and Cbfib2.
Figure 9B:
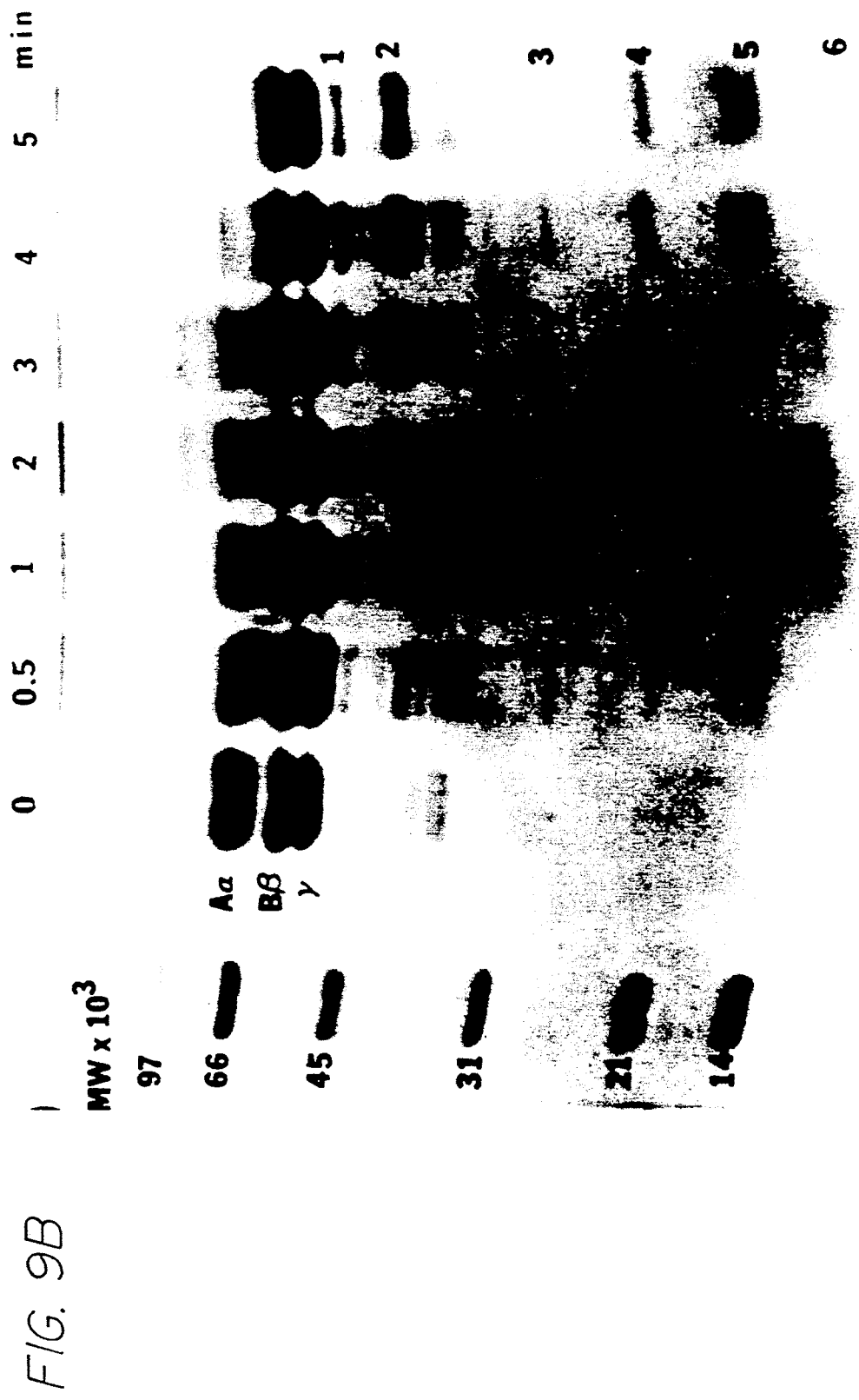

FIGS. 9 (A and B) show the events in the early phases of fibrinogen degradation by Cbfib1.1 (FIG. 9A) and Cbfib2 (FIG. 9B); time-course analysis (1–5 minutes) was effected using SDS-PAGE (10% acrylamide gels). It is apparent that at the ratio of substrate to enzyme selected (50/1), there is no difference in the rate of Aα-chain and Bβ-chain digestion for Cbfib1.1. The major product of the digestion for Cbfib1.1 is a polypeptide of molecular weight 45,000 (product 2). It is also evident that the same product is present in very low amounts in Cbfib2 (product 1). Cbfib2 also produces a group of breakdown products of molecular weight 38,000 (product 2) which are present in substantially lower amounts in the Cbfib1.1 fibrinogen digest. Fibrinopeptides at molecular weights of approximately 25,000, 20,000 and 15,000 are produced by both enzymes, but the 25,000 fragment (product 4) is very short-lived in the Cbfib1.1 digest. The 20,000 fragment (product 4) appears to accumulate after Cbfib2 digestion but is further degraded by Cbfib1.1 (product 5). An extra fragment of molecular weight 28,000 is produced in the Cbfib1.1 digest (product 3) which has no detectable equivalent in Cbfib2. A number of peptides of approximately 12 kDa are evident in the Cbfib2 fibrinogen digestion (product 7).

From the increased intensity with time of the band in the γ-chain region at 50 kDa in the Cbfib1.1 digest (FIG. 9A), it would appear that the Bβ-chain degradation product comigrates with the γ-chain on SDS-PAGE (product 1). Since there is no evident decrease in intensity of this component during the course of this experiment, it would appear that this fragment is not further degraded. The 50 kDa peptide was assumed to be a Bβ-derived product since comparison with Accfib indicates that the major product at 45 kDa (product 2) is derived from the Aα-chain (Cbfib1.1 digests the Aα-chain in a similar manner to Accfib). Further, Cbfib2 which degrades the Bβ-chain very slowly does not contain a digestion product which comigrates with the γ-chain.

In order to determine the sites of the initial cleavages in fibrinogen, larger amounts of fibrinogen (30 nmol) were incubated with Cbfib1.1 and Cbfib2 at a molar ratio of 50:1 (a ratio constant throughout the test experiments) for 1 minute and 2 minutes, respectively. The resultant cleavage products were then isolated. The short incubation times were employed based on the results of the previous experiment (shown in FIGS. 9(A and B)) as being optimal for the accumulation of early degradation products.

Figure 10A:
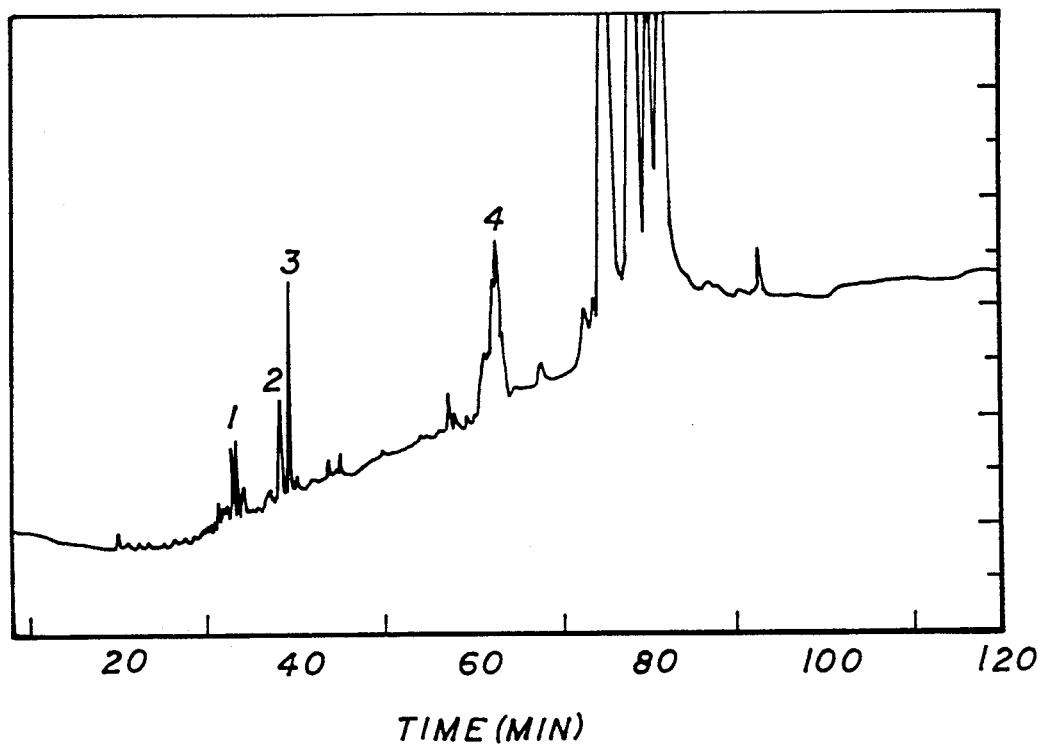
FIGS. 10(A and B) illustrate the results of reverse-phase chromatographic analysis of a Cbfib1.1 digest of fibrinogen.
Figure 10B:
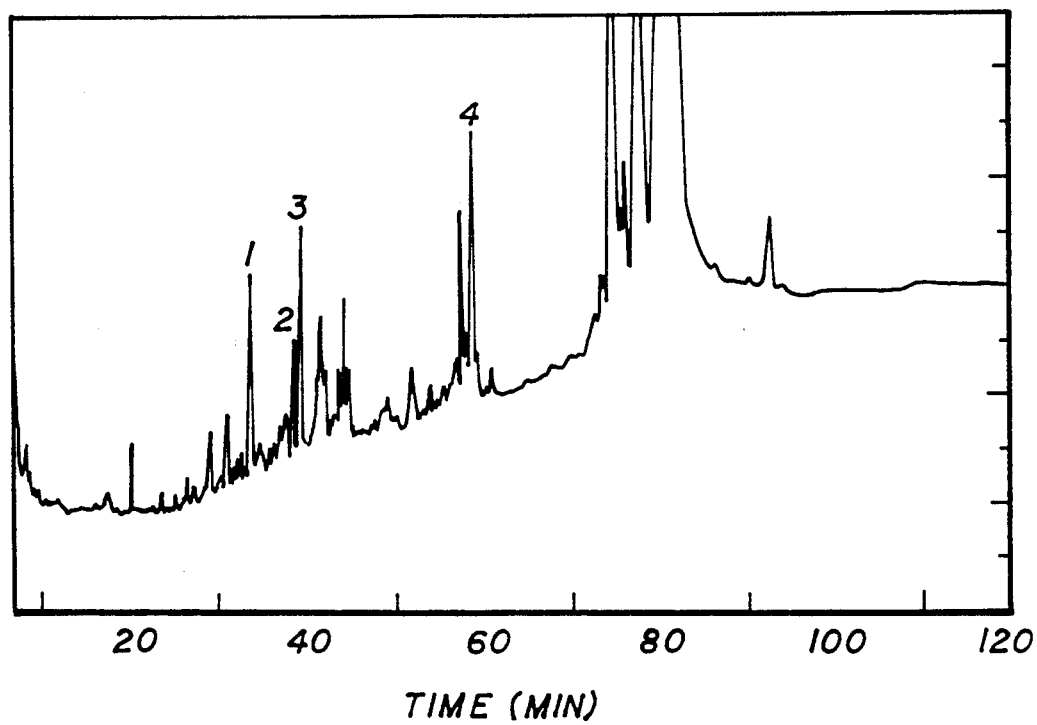

Following digestion the reactions were stopped by the addition of EDTA and samples were reduced and carboxymethylated. The Cbfib1.1 and Cbfib2 digests were analyzed by reverse phase chromatography (FIGS. 10(A and B) and 11(A and B) respectively). Following digestion of fibrinogen and reductive carboxymethylation of the digestion products as previously described, 100 μl of the respective digests were separated by the following elution protocol: 0–5 minutes isocratic elution with 90% solvent A (0.1% TFA in $H_2O$)–10% solvent B (0.1% TFA in 80% acetonitrile, 20% $H_2O$); 115 minutes linear gradient to 80% solvent B. FIG. 10A illustrates the results after 1 minute of incubation of Cbfib1.1 with fibrinogen; FIG. 10B, after 5 minutes of incubation. FIG. 11A illustrates the results after 2 minutes of incubation of Cbfib2 with fibrinogen; FIG. 11B, after 5 minutes of incubation. Numbered peptides were collected and further purified by reverse-phase chromatography on a Vydac $C_{18}$ column by the following elution protocol: 0–5 minutes isocratic elution with 90% solvent A, 10% solvent B; 60 minutes linear gradient to 80% solvent B. The amino-terminal sequences were then determined, as reported in Table III; a question mark indicates that the amino acid was not identified in the sequence.

Sequence analysis of the products of digestion suggest that Cbfib1.1 cleaves the Aα-chain at $Lys^{413}$-$Leu^{414}$ (peptide 1 in Table III and FIG. 10), $Ser^{505}$-$Thr^{506}$ (peptide 2) and $Tyr^{560}$-$Ser^{561}$ (peptide 3). The $Lys^{413}$-$Leu^{414}$ cleavage site has been identified as primary Accfib cleavage site in the Aα-chain of fibrinogen as well. The two other cleavage sites are quite unusual for a zinc-dependent enzyme. The sequence of fragment 4 corresponds to the sequence of the amino-terminus of the Bβ-chain of fibrinogen. The molecular weight of this fragment, as determined by SDS-PAGE, is approximately 9–10 kDa. It is obvious, therefore, that the cleavage site in the Bβ-chain is close to the amino-terminus.

Sequence analysis of the cleavage products derived following Cbfib2 incubation with fibrinogen reveals that the major cleavage sites are located in the Aα-chain at $Pro^{516}$-$Met^{517}$ (peptide 1, Table III and FIG. 11), and $Gly^{254}$-$Ser^{255}$ (peptide 2). Peptides 2 and 3 (Table III) have the same amino-terminal sequence but molecular weights of 10 and 40 kDa, respectively. The small size of peptide 2 suggests the possibility that Cbfib2 catalyzes another cleavage in the Aα-chain between residues 330–360, although this fragment has not yet been identified. Based on previous findings with Accfib digestion of fibrinogen, the 45 kDa fibrinogen fragment (although not sequenced) results from digestion of the Aα-chain by Cbfib2 at $Lys^{413}$-$Leu^{414}$. This fragment is produced in small amounts following Cbfib2 digestion (FIG. 9B, product 1), suggesting that cleavage occurs slowly at the $Lys^{413}$-$Leu^{414}$ position. Cleavage sites in the Aα-chain of fibrinogen are summarized in Table IV; the position of the amino acids was assigned using the terminology of Schechter and Berger [Schechter, I. and Berger, A., *Biochem. Biophys. Res. Commun.* 27:157–162 (1967)].

These findings indicate that Cbfib1.1 and Cbfib1.2, are not only structurally related, but they also cleave similar peptide bonds in fibrin and fibrinogen. The main difference from other fibrinolytic metalloproteinases studied to date, including atroxase from *Crotalus atrox*

(western diamondback rattlesnake) and fibrolase (Accfib) from *Agkistrodon contortrix contortrix* (southern copperhead) venoms, is that the *C. b. basiliscus* enzymes cleave the Bβ-chain of fibrinogen almost as readily as the Aα-chain. In fact at molar ratios of 1/50 (enzyme/substrate) there is no apparent difference in degradation rates between the Aα- and Bβ-chains. Interestingly, atroxase and fibrolase cleave the Aα-chain preferentially; the Bβ-chain is degraded subsequently. By contrast, following one hour incubation, the fibrinolytic enzyme from *Agkistrodon contortrix mokasen* (northern copperhead) venom degrades only the Aα-chain [Moran, J. B. and Geren, C. R., *Biochim. Biophys.* Acta 659:161–168 (1981)]. The venom fibrinolytic enzymes studied thus far exhibit virtually no hydrolytic activity on the γ-chain of fibrinogen.

Immunological (Western) blotting showed that the antibody to Accfib reacted very weakly with purified Cbfib1.1 or Cbfib2 [Chen, H. M. et al., *Toxicon* 29:683–694 (1991)]. This suggests that the enzymes, although structurally related and most likely belonging to the same family of low molecular weight snake venom metalloproteinases, may be immunologically distinct.

With fibrin as substrate, Cbfib1.1 and Cbfib1.2 exhibit a considerably slower degradation of the β-chain compared to the α-chain, probably due to steric hindrance induced by γ-chain cross-linking. Nonetheless, the rate of β-chain digestion is more rapid than that produced by Accfib under identical incubation conditions (1/50 molar ratio of venom fibrinolytic enzyme to substrate). Cbfib1.1 and Cbfib1.2 also show a broader specificity of cleavage sites than Accfib, although Lys$^{413}$-Leu$^{414}$, the primary cleavage site of Accfib in the α-chain of fibrinogen and fibrin is among these sites. In view of the broader specificity on fibrinogen displayed by the *C. b. basiliscus* enzymes, it is surprising that these enzymes possess lower general proteolytic (azocaseinolytic) activity than Accfib (FIG. 6). Lower activity towards the general protease substrate azocasein may signify a higher degree of specialization towards fibrin/fibrinogen than Accfib.

Cbfib2 varies significantly both structurally and functionally from Cbfib1.1 and Cbfib1.2, although, like the other enzymes, it is also a metalloproteinase. Fibrinolytic activity of Cbfib2 is confined mainly to the α-chain of fibrin and fibrinogen, like Accfib. However, unlike Accfib it shows only limited cleavage of Lys$^{413}$-Leu$^{414}$ bond indicating structural differences in the active site geometry. Surprisingly, Cbfib2 possess significantly higher levels of general proteolytic (azocaseinolytic) activity, approximately 8 to 12-fold higher, than the other enzymes studied (FIG. 6B). This increased proteolytic activity is not evidenced by increased hemorrhagic activity since Cbfib2, as well as Cbfib1.1 and Cbfib1.2, showed no such activity following subcutaneous injection of large amounts of the enzymes (50–100 μg) into the backs of anesthetized mice. Hemorrhagic activity is defined as the ability to cause local hemorrhaging following intradermal injection of venom fractions into the backs of depilated laboratory animals.

Recently, two hemorrhagic proteinases, B1 and B2, were purified and characterized from *C. b. basiliscus* venom [Molina, O. et al., *Int'l J. Biochem.* 22:253–261 (1990)]. B1 has a molecular weight of 27,000 and pI of 9.8, whereas B2 has a molecular weight of 27,500 and pI of 5.3. Both proteins are inhibited by EDTA and degrade fibrin and fibrinogen, but they do not cross-react antigenically. Although appearing to be very similar to the fibrinolytic enzymes described herein, they must be different because the fibrinolytic enzymes of the present invention possess virtually no hemorrhagic activity. Whether the hemorrhagic proteinases were contaminated by very similar fibrinolytic enzymes remains to be determined. Cbfib1.1 and Cbfib1.2 appear similar to hemorrhagic proteinase B2, which has a low isoelectric point, and Cbfib2 appears similar to B1, which has a high isoelectric point and slightly lower molecular weight. Additionally, Cbfib1.1 and Cbfib1.2 and hemorrhagic proteinase B2 hydrolyze Aα-and Bβ-chains of fibrinogen quite rapidly.

Venom hemorrhagic proteinases have been shown to degrade components of the extracellular matrix as well as fibrinogen. Interestingly, hemorrhagic proteinases from several shake venoms are relatively small metalloproteinases processing striking amino acid sequence similarity, not only amongst their own members [Shannon, J. D. et al., *J. Biol. Chem.* 264:11575–11583 (1989); Miyata, T. et al., *J. Biochem.* 105:847–853 (1989); Takeya, H. et al., *J. Biochem.* 106:151–157 (1990)], but also with the fibrinolytic metalloproteinases from southern copperhead venom and with other non-hemorrhagic venom metalloproteinases. Based on the similarities of their physicochemical and biological properties, it is suspected that the *C.b.basiliscus* enzymes are also members of the same family as the venom metalloproteinases of known sequence, including fibrinolytic and hemorrhagic enzymes. All of these enzymes contain the sequence: His-Glu-Xaa-Gly-His-Asn-Leu-Gly (where Xaa is the hydrophobic residue leucine, isoleucine, or methionine). The signature sequence contains the putative zinc-chelating residues (two histidine residues separated by three amino acids) and the catalytic glutamic acid residue (Takeya et al., supra) identified by homology with the zinc-chelating sequence of thermolysin [Coleman, P. M. et al., *J. Mol. Biol.* 70:701–724 (1972)]. However, the difference in kinetics of inhibition of the venom metalloproteinases by Zincov as compared to thermolysin (a zinc-dependent, bacterial fibrinolytic metalloproteinase) is considerable ($K_i$ for thermolysin is 0.48 μM), suggesting that the zinc atom may be oriented differently in the active cite of the venom fibrinolytic enzymes.

Amino acid analysis suggests that the Cbfib enzymes contain approximately 210 residues. By contrast the venom metalloproteinases of known sequence contains 201–203 amino acids, with evidence of sequence microheterogeneity at the amino-terminus. Accfib contains 203 amino acids. It would appear, therefore, that there is a family of evolutionarily related venom metalloproteinases distributed widely throughout different genera of the Crotalidae family, including Agkistrodon, Trimeresurus, and Crotalus, and perhaps even more widely in other snake families. These small metalloproteinases possess strikingly similar sequences and physicochemical properties, but have different biological activities. These findings suggest that some of the functionally critical amino acids are to be found not in those residues that are conserved across evolutionary lines, but rather in the amino acids that differ from one enzyme to another.

Analysis of the primary structure around the peptide bonds cleaved in fibrinogen by the fibrinolytic enzymes from *C. b. basiliscus* venom from the P$_7$ to the P$_7$' subsites (Table IV) fails to show a requirement for any preferred amino acid residues that determine cleavage specificity. The only possible pattern emerging is the presence of threonine or serine (hydroxyl amino acids) in the $P_3$ subsite for Cbfib1.1. These findings suggest that bond cleavage specificity must be guided at least in part by secondary and tertiary structure determinants in large substrates such as fibrinogen. The fibrinolytic enzymes from *C. b. basiliscus* venom appear to exhibit quite unusual bond cleavage specificity using what can be considered a natural substrate, fibrin or fibrinogen. Cbfib1.1 cleaves at the same $Lys^{413}$-$Leu^{414}$ bond in the Aα-chain of fibrinogen as fibrolase, the fibrinolytic enzyme from southern copperhead venom. However, additional cleavages occur at $Ser^{505}$-$Thr^{506}$ and $Tyr^{560}$-$Ser^{561}$ in the Aα-chain. Cleavage sites catalyzed by Cbfib2 are also unusual: $Pro^{516}$-$Met^{517}$ and $Gly^{254}$-$Ser^{255}$ in the Aα-chain of fibrinogen. To establish the sites of cleavage, the unambiguous amino-terminal sequences of the fibrinogen degradation peptides were determined and the siscile bonds were then deduced from the known sequence of the Aα-chain of human fibrinogen [Henschen, A. et al., *Ann. N.Y. Acad. Sci.* 408:28-43 (1983)].

The advantage of the fibrinolytic enzymes described herein is that their action is not dependent on plasminogen activation, and their disadvantages are no worse than those of streptokinase, the use of which is gaining momentum in thrombolytic therapy. Additionally, the venom-derived enzymes may act synergistically with plasminogen activators, thereby providing an intriguing potential clinical application for these enzymes. Further structural studies of these enzymes will elucidate their mode of action, and information derived may be used in thrombolytic agent design.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

TABLE I

| Purification Step | Fibrinolytic Enzyme Purification | | | | |
|---|---|---|---|---|---|
| | Protein (mg) | Activity (P.I.U) | Specific Activity (P.I.U./mg) | Purification | Recovery (% crude activity) |
| Crude | 579 | 89 | .15 | 0 | 100 |
| After hydrophobic interaction chromatography | | | | | |
| Cbfib1* | 241 | 74 | .31 | 2.1 | 83 |
| Cbfib2 | 32 | 5.6 | .17 | 1.1 | 6.3 |
| After hydroxylapatite chromatography | | | | | |
| Cbfib1.1 | 83 | 33.7 | .41 | 2.7 | 37.8 |
| Cbfib1.2 | 42 | 18.5 | .44 | 2.9 | 20.1 |
| Cbfib2** | 7 | 3.5 | .50 | 3.3 | 3.9 |
| After AX-300 chromatography | | | | | |
| Cbfib1.1 | 58 | 27.6 | .47 | 3.1 | 31 |
| Cbfib1.2 | 34 | 17.1 | .50 | 3.3 | 19.2 |

*At this step Cbfib1.1 and Cibfib1.2 eluted together.
**After this step Cbfib2 was homogeneous.

TABLE II

| Amino Acid Compositions of Fibrinolytic Enzymes | | | |
|---|---|---|---|
| Amino Acid | Cbfib1.1 | Cbfib1.2 | Cbfib2 |
| Asp | 27 | 26 | 25 |
| Glu | 22 | 20 | 21 |
| Ser | 21 | 20 | 18 |
| Gly | 14 | 12 | 15 |
| His | 9 | 9 | 8 |
| Arg | 15 | 15 | 14 |
| Thr | 12 | 11 | 11 |
| Ala | 11 | 9 | 15 |
| Pro | 8 | 7 | 8 |
| Tyr | 10 | 12 | 11 |
| Val | 13 | 19 | 13 |
| Met | 5 | 5 | 6 |
| Ile | 11 | 11 | 10 |
| Leu | 20 | 21 | 19 |
| Phe | 6 | 6 | 6 |
| Lys | 7 | 8 | 10 |
| Cys | N.D. | N.D. | N.D. |
| Trp | N.D. | N.D. | N.D. |
| Sum | 211 | 211 | 211 |

TABLE III

| | N-terminal amino acid sequence of fibrinogen degradation products following digestion with Cbfib1.1 or Cbfib2 |
|---|---|
| Peptide Number | Amino-terminal sequence of fibrinogen fragment |
| Cbfib1.1 digestion | |
| 1 | Leu—Val—Thr—Ser—Lys—Gly—Asp—?—Lys— |
| 2 | Thr—Gly—Lys—Asn—?—?—Gly—Phe—Phe—Ser— |
| 3 | Ser—Lys—Gln—Phe—Thr—Ser—?—?—?—Tyr— |
| 4 | ?—Gly—Val—Asn—Asp—Asn—Glu |
| Cbfib2 digestion | |
| 1 | Met—Leu—Gly—Glu—Phe—Val—Ser—Glu—?—Glu—?—?—Gly—Ser— |
| 2 | Ser—Thr—Ser—?—Gly—Thr—Gly—?—?—?—Glu— |

TABLE III-continued

N-terminal amino acid sequence of fibrinogen degradation products following digestion with Cbfib1.1 or Cbfib2

| Peptide Number | Amino-terminal sequence of fibrinogen fragment |
|---|---|
| 3 | Ser—Thr—Ser—?—Gly—?—Gly—Gly—?—Glu— |

TABLE IV

Primary Structure of Aα-chain of Fibrinogen Cleavage Sites For Cbfib1.1 and Cbfib1.2 Covering the $P_7$ to the $P_7'$ Subsites

| | $P_7$ | $P_6$ | $P_5$ | $P_4$ | $P_3$ | $P_2$ | $P_1$ | $P_1'$ | $P_2'$ | $P_3'$ | $P_4'$ | $P_5'$ | $P_6'$ | $P_7'$ |
|---|---|---|---|---|---|---|---|---|---|---|---|---|---|---|
| Cbfib1.1 cleavage sites in the Aα-chain of fibrinogen | | | | | | | | | | | | | | |
| Site 1 (residues 407–420) | R | E | Y | H | T | E | K | L | V | T | S | K | G | D |
| Site 2 (residues 499–512) | A | F | F | D | T | A | S | T | G | K | T | F | P | G |
| Site 3 (residues 554–567) | R | G | K | S | S | S | Y | S | K | Q | F | T | S | S |
| Cbfib2 cleavage sites in the Aα-chain of fibrinogen | | | | | | | | | | | | | | |
| Site 1 (residues 510–523) | F | P | G | F | F | S | P | M | L | G | E | F | V | S |
| Site 2 (residues 248–261) | N | E | I | T | R | G | G | S | T | S | Y | G | T | G |

What is claimed is:

1. A substantially pure zinc metalloproteinase as derived from venom of *Crotalus basiliscus basiliscus* and having an activity profile characterized selectively cleaving the Aα-chain of fibrinogen at at least one cleavage site selected from the group consisting of $Ser^{505}$-$Thr^{506}$ and $Tyr^{560}$-$Ser^{561}$ by:

direct fibrinolytic activity in plasminogen free systems and no detectable plasminogen activation activity in vitro;

no systemic toxicity in vivo as exemplified by the absence of hemorrhagic activity; and degradation of the Aα- and Bβ-chains of fibrinogen at comparable rates, wherein said metalloproteinase is selected from the group consisting of Cbfib1.1 having an isoelectric point at about pH 4.1, and Cbfib1.2 having an isoelectric point at about pH 4.7.

2. A metalloproteinase according to claim 1, further characterized by a general protease activity which is less than about 70% of Accfib.

3. A metalloproteinase according to claim 1, which is Cbfib1.1.

4. A metalloproteinase according to claim 1, which is Cbfib1.2.

5. A metalloproteinase according to claim 1, further characterized by weak cross-reactivity with antibodies generated against Accfib.

6. A substantially pure zinc metalloproteinase as derived from venom of *Crotalus basiliscus basiliscus* and having an activity profile characterized selectively cleaving the Aα-chain of fibrinogen at at least one cleavage site selected from the group consisting of $Pro^{516}$-$Met^{517}$ and $Gly^{254}$-$Ser^{255}$ by:

direct fibrinolytic activity in plasminogen free systems and no detectable plasminogen activation activity in vitro;

no systemic toxicity in vivo as exemplified by the absence of hemorrhagic activity; and preferential degradation of the Aα-chain of fibrinogen relative to the Bβ-chain and absence of a digestion product which comigrates with the γ-chain, wherein said metalloproteinase is Cbfib2 having an isoelectric point at about pH 8.5.

7. A metalloproteinase according to claim 6, further characterized by weak cross-reactivity with antibodies generated against Accfib.

8. A method for dissolving blood clots in a patient in need of such treatment, comprising administering an effective amount of a substantially pure zinc metalloproteinase as derived from venom of *Crotalus basiliscus basiliscus* and to said patient, said metalloproteinase having an activity profile characterized selectively cleaving the Aα-chain of fibrinogen at at least one cleavage site selected from the group consisting of $Ser^{505}$-$Thr^{506}$ and $Tyr^{560}$-$Ser^{561}$ by:

direct fibrinolytic activity in plasminogen free systems and no detectable plasminogen activation activity in vitro;

no systemic toxicity in vivo as exemplified by the absence of hemorrhagic activity; and degradation of the Aα- and Bβ-chains of fibrinogen at comparable rates, wherein said metalloproteinase is selected from the group consisting of Cbfib1.1 having an isoelectric point at about pH 4.1, and Cbfib1.2 having an isoelectric point at about pH 4.7.

9. A method according to claim 8, wherein said metalloproteinase is administered at a concentration in the range of about 0.1 to about 2.0 mg/ml in a physiologically acceptable solution.

* * * * *

UNITED STATES PATENT AND TRADEMARK OFFICE
CERTIFICATE OF CORRECTION

PATENT NO. : 5,260,060
DATED : November 9, 1993
INVENTOR(S) : Fancis S. Markland, Jr., et al.

It is certified that error appears in the above-identified patent and that said Letters Patent is hereby corrected as shown below:

Column 1, line 2, after the title please insert:

--This invention was made with government support under Contract No. 5K04 HL00869-05 awarded by the National Institutes of Health. The government has certain rights in the invention.--

Signed and Sealed this

Twenty-second Day of June, 1999

Attest:

Q. TODD DICKINSON

Attesting Officer

Acting Commissioner of Patents and Trademarks